US012416028B2

(12) United States Patent
Chen et al.

(10) Patent No.: US 12,416,028 B2
(45) Date of Patent: Sep. 16, 2025

(54) BIOSYNTHETIC PRODUCTION OF GAMMA- AND DELTA-LACTONES USING CYTOCHROME P450 ENZYMES HAVING SUBTERMINAL HYDROXYLASE ACTIVITY

(71) Applicant: Conagen Inc., Bedford, MA (US)

(72) Inventors: Hui Chen, North Billerica, MA (US); Xiaodan Oliver Yu, Lexington, MA (US)

(73) Assignee: Conagen Inc., Bedford, MA (US)

( * ) Notice: Subject to any disclaimer, the term of this patent is extended or adjusted under 35 U.S.C. 154(b) by 558 days.

(21) Appl. No.: 17/480,177

(22) Filed: Sep. 21, 2021

(65) Prior Publication Data

US 2022/0106618 A1 Apr. 7, 2022

Related U.S. Application Data

(63) Continuation of application No. PCT/US2020/024071, filed on Mar. 21, 2020.

(60) Provisional application No. 62/821,894, filed on Mar. 21, 2019.

(51) Int. Cl.

| | |
|---|---|
| ***C12P 17/06*** | (2006.01) |
| ***C07D 309/30*** | (2006.01) |
| ***C12N 1/16*** | (2006.01) |
| ***C12N 1/20*** | (2006.01) |
| ***C12N 9/02*** | (2006.01) |
| ***C12P 7/62*** | (2022.01) |
| ***C12P 17/04*** | (2006.01) |

(52) U.S. Cl.

CPC ................ *C12P 17/06* (2013.01); *C12N 1/16* (2013.01); *C12N 1/20* (2013.01); *C12P 17/04* (2013.01); *C07D 309/30* (2013.01); *C12N 9/0071* (2013.01); *C12P 7/62* (2013.01)

(58) Field of Classification Search

CPC .. C12P 17/06; C12P 17/04; C12P 7/62; C12N 1/16; C12N 1/20; C12N 9/0071; C12N 15/70; C12N 9/0042; C07D 309/30; C12Y 101/01042

See application file for complete search history.

(56) References Cited

U.S. PATENT DOCUMENTS

| | | | | |
|---|---|---|---|---|
| 5,032,513 | A * | 7/1991 | Page | C12P 17/06 435/126 |
| 7,524,664 | B2 * | 4/2009 | Arnold | C12N 9/0077 435/71.1 |
| 9,970,037 | B2 | 5/2018 | Tang et al. | |
| 11,549,131 | B2 * | 1/2023 | Chen | C12P 17/04 |
| 2005/0130278 | A1 | 6/2005 | Mitsuhashi et al. | |
| 2008/0293101 | A1 | 11/2008 | Peters et al. | |
| 2010/0285546 | A1 | 11/2010 | Liao et al. | |
| 2021/0261991 | A1 | 8/2021 | Chen et al. | |

FOREIGN PATENT DOCUMENTS

| | | | | |
|---|---|---|---|---|
| WO | WO 2009/030672 A1 | | 3/2009 | |
| WO | WO-2017137935 A1 | * | 8/2017 | C12N 15/52 |
| WO | WO 2018/046104 A1 | | 3/2018 | |
| WO | WO 2020/018729 A1 | | 1/2020 | |

OTHER PUBLICATIONS

Romero-Guido C. et al., "Biochemistry of lactone formation in yeast and fungi and its utilization for the production of flavour and fragrance compounds, Appl Microbiol Biotechnol (2011) 89: pp. 535-547." DOI: 10.1007/s00253-010-2945-0 (Year: 2011).*

Krzyczkowska et al., "Lactone formation in yeast and fungi. Fungal Metabolites, (2017): pp. 461-498." DOI: 10.1007/978-3-319-25001-4_13 (Year: 2017).*

Kitazume et al. "Kinetic analysis of hydroxylation of saturated fatty acids by recombinant P450foxy produced by an *Escherichia coli* expression system. European journal of biochemistry vol. 269,8 (2002): pp 2075-2082." DOI: 10.1046/j.1432-1033.2002.02855.x (Year: 2002).*

Baker et al. "Expression, Purification, and Biochemical Characterization of the Flavocytochrome P450 CYP505A30 from Myceliophthora thermophila. ACS omega vol. 2,8 (2017): pp 4705-4724." DOI: 10.1021/acsomega.7b00450 (Year: 2017).*

Nykiel-Szymanska et al., "Elinimation and detoxification of 2,4-D by Umbelopsis isabelline with the involvement of cytochrome P450, Environ Sci Pollut Res (2018) pp. 2738-2743", submitted with the IDS Dec. 23, 2021 (Year: 2018).*

Berka et al., Comparative genomic analysis of the thermophilic biomass-degrading fungi *Myceliophthora thermophila* and *Thielavia terrestris*. Nat Biotechnol. Oct. 2, 2011;29(10):922-7. doi: 10.1038/nbt.1976.

Dietrich et al., Altering the regioselectivity of the subterminal fatty acid hydroxylase P450 BM-3 towards gamma- and delta-positions. J Biotechnol. Jan. 1, 2009;139(1):115-7. doi: 10.1016/j.jbiotec.2008.10.002. Epub Oct. 15, 2008.

Endrizzi et al., Bioconversion of methyl ricinoleate to 4-hydroxy-decanoic acid and to gamma-decalactone by yeasts of the genus *Candida*. J Basic Microbiol. 1995;35(5):285-92. doi: 10.1002/jobm.3620350503.

Genbank Submission. NCBI; Accession No. ORZ20503, Version ORZ20503.1. cytochrome P450 [Absidia repens]. Mondo et al; Apr. 20, 2017. 2 pages.

(Continued)

*Primary Examiner* — Terry A McKelvey
*Assistant Examiner* — Andrew T Moehlman
(74) *Attorney, Agent, or Firm* — Wolf, Greenfield & Sacks, P.C.

(57) ABSTRACT

Provided herein are methods for making lactones comprising incubating a cellular system expressing a heterologous cytochrome P450 (CYP450) protein with a medium comprising straight chain fatty acids to produce subterminal hydroxy fatty acids, and incubating a yeast cell culture with the subterminal hydroxy fatty acids to produce lactones.

17 Claims, 11 Drawing Sheets

Specification includes a Sequence Listing.

(56) References Cited

OTHER PUBLICATIONS

Genbank Submission. NCBI; Accession No. XP_003663647, version XP_003663647.1. Uncharacterized protein MYCTH_101224 [Thermothelomyces thermophiles ATCC 42464]. Berka et al.; Nov. 27, 2019. 12 Pages.

Nagel et al., Diverging Mechanisms: Cytochrome-P450-Catalyzed Demethylation and γ-Lactone Formation in Bacterial Gibberellin Biosynthesis. Angew Chem Int Ed Engl. May 22, 2018;57(21):6082-6085. doi: 10.1002/anie.201713403. Epub Apr. 26, 2018.

Nykiel-Szymańska et al., Elimination and detoxification of 2,4-D by Umbelopsis isabellina with the involvement of cytochrome P450. Environ Sci Pollut Res Int. Jan. 2018;25(3):2738-2743. doi: 10.1007/s11356-017-0571-4. Epub Nov. 14, 2017.

* cited by examiner

SEQUENCE LISTING

<160> NUMBER OF SEQ ID NOS: 8

<210> SEQ ID NO 1
<211> LENGTH: 3243
<212> TYPE: DNA
<213> ORGANISM: Myceliophthora thermophila

<400> SEQUENCE: 1

```
atggcggata agaccaccga aaccgtgccg attccgggtc cgccgggcct gccgctggtt     60
ggtaatgcgc tggcgtttga tagcgaactg ccgctgcgta ccttccagga atttgcggag    120
gaatacggcg agatctatcg tctgaccctg ccgaccggta ccaccctggt ggttagcagc    180
caagcgctgg ttcacgaact gtgcgacgat aagcgtttca agaagccggt tgctgcggcg    240
ctggcggaag tgcgtaacgg cgttaacgac ggtctgttta ccgcgcgtga agaggagccg    300
aactggggca tcgcgcaccg tattctgatg ccggcgtttg gtccggcgag cattcagggc    360
atgtttaccg aaatgcacga gatcgcgagc caactggcgc tgaaatgggc gcgtcacggt    420
ccggacaccc cgattttcgt taccgacgat tttacccgtc tgaccctgga taccctggcg    480
ctgtgcacca tgaacttccg ttttaacagc tactatcacg acgaactgca cccgttcatc    540
aacgcgatgg gcaactttct gaccgagagc ggtgcgcgtg cgatgcgtcc ggcgatcacc    600
agcattttcc accaggcggc gaaccgtaag tactgggaag atattgaggt tctgcgtaaa    660
accgcgcaag gtgtgctgga cacccgtcgt aagcacccga ccaaccgtaa agatctgctg    720
agcgcgatgc tggacggcgt ggatgcgaaa accggtcaga aactgagcga cagcagcatc    780
attgataacc tgatcacctt tctgattgcg ggccacgaaa ccaccagcgg tctgctgagc    840
ttcgcgtttt acctgctgat taagcaccag gacgcgtatc gtaaagcgca agaagaggtg    900
gatcgtgtta tcggcaaggg cccgattaaa gttgaacaca tcaagaaact gccgtacatc    960
gcggcggtgc tgcgtgaaac cctgcgtctg tgcccgacca ttccgatcat taaccgtgcg   1020
gcgaagcagg acgaagttat cggtggcaag tacgcggtgg cgaaagatca gcgtctggcg   1080
ctgctgctgg cgcaaagcca cctggacccg gcggtttatg gcgaaaccgc gaagcaattc   1140
attccggagc gtatgctgga cgaaaacttt gagcgtctga accgtgagta tccggattgc   1200
tggaaaccgt tcggtaccgg catgcgtgcg tgcatcggtc gtccgtttgc gtggcaggaa   1260
gcggtgctgg ttatggcgat gctgctgcaa aacttcgact ttgttctgca cgatccgtac   1320
tatgagctgc actacaagca gaccctgacc accaagccga aagacttcta tatgcgtgcg   1380
atcctgcgtg atggcctgac cgcgaccgaa ctggagcacc gtctggcggg taacgcggcg   1440
agcgtggcgc gtagcggtgg cggtggcggt ggcccgagca aaccgaccgc gcagaaaacc   1500
agcccggcgg aagcgaaacc gatgagcatc ttctacggca gcaacaccgg tacctgcgag   1560
agcctggcgc aacgtctggc gaccgatgcg gcgagccacg gttatgctgc ggcggcggtg   1620
gaaccgctgg acaccgcgac cgagaagctg ccgaccgatc gtccggtggt tatcattacc   1680
gcgagcttcg agggtcagcc gccggacaac gcggcgaagt tttgcggctg gctgaaaaac   1740
ctggaaggtg atgagctgaa aaacgtgagc tacgcggttt tcggttgcgg ccaccacgac   1800
tggagccaga cctttcaccg tattccgaag ctggttcacc aaaccatgaa agcgcacggt   1860
gcgagcccga tctgcgacga aggcctgacc gatgtggcgg agggtaacat gttcaccgat   1920
tttgaacaat gggaggacga tgtgttctgg ccggcggttc gtgcgcgtta tggcgcggcg   1980
ggtgcggttg cggaaaccga ggacgcgccg ggtagcgatg gtctgaacat ccactttagc   2040
agcccgcgta gcagcaccct gcgtcaggac gtgcgtgaag cgaccgtggt tggtgaagcg   2100
```

```
ctgctgaccg cgccggatgc gccgccgaag aaacacattg aagttcaact gccggacggc   2160

gcgacctaca aagtgggtga ttatctggcg gtgctgccgg ttaacagcaa ggagagcatt   2220

ggtcgtgtta tgcgtaaatt ccagctgagc tgggacagcc acgtgaccat cgcgagcgat   2280

cgttggaccg cgctgccgac cggtaccccg gtgccggcgt acgacgttct gggtagctat   2340

gtggagctga gccaaccggc gaccaaacgt ggtatcctgc gtctggcgga tgcggcggaa   2400

gatgaggcga ccaaggcgga actgcaaaaa ctggcgggtg atctgtacac cagcgagatt   2460

agcctgaaac gtgcgagcgt tctggacctg ctggatcgtt tcccgagcat cagcctgccg   2520

ttcggtacct ttctgagcct gctgccgccg attcgtccgc gtcaatacag catcagcagc   2580

agcccgctga acgacccgag ccgtgcgacc ctgacctata gcctgctgga tagcccgagc   2640

ctggcgaacc cgagccgtcg tttcgtgggc gttgcgacca gctacctgag cagcctggtt   2700

cgtggtgaca agctgctggt gagcgttcgt ccgacccaca ccgcgtttcg tctgccggac   2760

gaagataaaa tgggtgaaac cgcgatcatt tgcgtgggtg cgggtagcgg tctggcgccg   2820

ttccgtggtt ttatccagga acgtgcggcg ctgctggcga aaggtaccca actggcggcg   2880

gcgctgctgt tctacggttg ccgtagcccg gagaaggacg atctgtatcg tgacgaattc   2940

gataaatggc aagagagcgg tgcggtggat gttcgtcgtg cgtttagccg tgttgatagc   3000

gacgataccg aggcgcgtgg ttgccgtcac gttcaggacc gtctgtggca cgatcgtgaa   3060

gaggtgaagg cgctgtggga ccgtggcgcg cgtgtgtacg tttgcggtag ccgtcaagtg   3120

ggcgaaggtg ttaaaaccgc gatgggccgt atcgtgctgg gtgaagagga cgcggaggat   3180

gcgatcagca agtggtatga aaccgtgcgt aatgaccgtt atgcgaccga tgtgttcgac   3240

taa                                                                 3243
```

<210> SEQ ID NO 2
<211> LENGTH: 1251
<212> TYPE: DNA
<213> ORGANISM: Escherichia coli

<400> SEQUENCE: 2

```
atggaaagta aagtagttgt tccggcacaa ggcaagaaga tcaccctgca aaacggcaaa     60

ctcaacgttc ctgaaaatcc gattatccct tacattgaag gtgatggaat cggtgtagat    120

gtaaccccag ccatgctgaa agtggtcgac gctgcagtcg agaaagccta taaaggcgag    180

cgtaaaatct cctggatgga aatttacacc ggtgaaaaat ccacacaggt ttatggtcag    240

gacgtctggc tgcctgctga aactcttgat ctgattcgtg aatatcgcgt tgccattaaa    300

ggtccgctga ccactccggt tggtggcggt attcgctctc tgaacgttgc cctgcgccag    360

gaactggatc tctacatctg cctgcgtccg gtacgttact atcagggcac tccaagcccg    420

gttaaacacc ctgaactgac cgatatggtt atcttccgtg aaaactcgga agacatttat    480

gcgggtatcg aatggaaagc agactctgcc gacgccgaga aagtgattaa attcctgcgt    540

gaagagatgg gggtgaagaa aattcgcttc ccggaacatt gtggtatcgg tattaagccg    600

tgttcggaag aaggcaccaa acgtctggtt cgtgcagcga tcgaatacgc aattgctaac    660

gatcgtgact ctgtgactct ggtgcacaaa ggcaacatca tgaagttcac cgaaggagcg    720

tttaaagact ggggctacca gctggcgcgt gaagagtttg gcggtgaact gatcgacggt    780

ggcccgtggc tgaaagttaa aaacccgaac actggcaaag agatcgtcat taaagacgtg    840

attgctgatg cattcctgca acagatcctg ctgcgtccgg ctgaatatga tgttatcgcc    900
```

```
tgtatgaacc tgaacggtga ctacatttct gacgccctgg cagcgcaggt tggcggtatc    960

ggtatcgccc ctggtgcaaa catcggtgac gaatgcgccc tgtttgaagc cacccacggt   1020

actgcgccga aatatgccgg tcaggacaaa gtaaatcctg gctctattat tctctccgct   1080

gagatgatgc tgcgccacat gggttggacc gaagcggctg acttaattgt taaaggtatg   1140

gaaggcgcaa tcaacgcgaa aaccgtaacc tatgacttcg agcgtctgat ggatggcgct   1200

aaactgctga aatgttcaga gtttggtgac gcgatcatcg aaaacatgta a            1251


<210> SEQ ID NO 3
<211> LENGTH: 1080
<212> TYPE: PRT
<213> ORGANISM: Myceliophthora thermophila

<400> SEQUENCE: 3

Met Ala Asp Lys Thr Thr Glu Thr Val Pro Ile Pro Gly Pro Pro Gly
1               5                   10                  15

Leu Pro Leu Val Gly Asn Ala Leu Ala Phe Asp Ser Glu Leu Pro Leu
            20                  25                  30

Arg Thr Phe Gln Glu Phe Ala Glu Glu Tyr Gly Glu Ile Tyr Arg Leu
        35                  40                  45

Thr Leu Pro Thr Gly Thr Thr Leu Val Val Ser Ser Gln Ala Leu Val
    50                  55                  60

His Glu Leu Cys Asp Asp Lys Arg Phe Lys Lys Pro Val Ala Ala Ala
65                  70                  75                  80

Leu Ala Glu Val Arg Asn Gly Val Asn Asp Gly Leu Phe Thr Ala Arg
                85                  90                  95

Glu Glu Glu Pro Asn Trp Gly Ile Ala His Arg Ile Leu Met Pro Ala
            100                 105                 110

Phe Gly Pro Ala Ser Ile Gln Gly Met Phe Thr Glu Met His Glu Ile
        115                 120                 125

Ala Ser Gln Leu Ala Leu Lys Trp Ala Arg His Gly Pro Asp Thr Pro
    130                 135                 140

Ile Phe Val Thr Asp Asp Phe Thr Arg Leu Thr Leu Asp Thr Leu Ala
145                 150                 155                 160

Leu Cys Thr Met Asn Phe Arg Phe Asn Ser Tyr Tyr His Asp Glu Leu
                165                 170                 175

His Pro Phe Ile Asn Ala Met Gly Asn Phe Leu Thr Glu Ser Gly Ala
            180                 185                 190

Arg Ala Met Arg Pro Ala Ile Thr Ser Ile Phe His Gln Ala Ala Asn
        195                 200                 205

Arg Lys Tyr Trp Glu Asp Ile Glu Val Leu Arg Lys Thr Ala Gln Gly
    210                 215                 220

Val Leu Asp Thr Arg Arg Lys His Pro Thr Asn Arg Lys Asp Leu Leu
225                 230                 235                 240

Ser Ala Met Leu Asp Gly Val Asp Ala Lys Thr Gly Gln Lys Leu Ser
                245                 250                 255

Asp Ser Ser Ile Ile Asp Asn Leu Ile Thr Phe Leu Ile Ala Gly His
            260                 265                 270

Glu Thr Thr Ser Gly Leu Leu Ser Phe Ala Phe Tyr Leu Leu Ile Lys
        275                 280                 285

His Gln Asp Ala Tyr Arg Lys Ala Gln Glu Glu Val Asp Arg Val Ile
    290                 295                 300

Gly Lys Gly Pro Ile Lys Val Glu His Ile Lys Lys Leu Pro Tyr Ile
305                 310                 315                 320
```

```
Ala Ala Val Leu Arg Glu Thr Leu Arg Leu Cys Pro Thr Ile Pro Ile
                325                 330                 335

Ile Asn Arg Ala Ala Lys Gln Asp Glu Val Ile Gly Gly Lys Tyr Ala
            340                 345                 350

Val Ala Lys Asp Gln Arg Leu Ala Leu Leu Leu Ala Gln Ser His Leu
        355                 360                 365

Asp Pro Ala Val Tyr Gly Glu Thr Ala Lys Gln Phe Ile Pro Glu Arg
    370                 375                 380

Met Leu Asp Glu Asn Phe Glu Arg Leu Asn Arg Glu Tyr Pro Asp Cys
385                 390                 395                 400

Trp Lys Pro Phe Gly Thr Gly Met Arg Ala Cys Ile Gly Arg Pro Phe
                405                 410                 415

Ala Trp Gln Glu Ala Val Leu Val Met Ala Met Leu Leu Gln Asn Phe
            420                 425                 430

Asp Phe Val Leu His Asp Pro Tyr Tyr Glu Leu His Tyr Lys Gln Thr
        435                 440                 445

Leu Thr Thr Lys Pro Lys Asp Phe Tyr Met Arg Ala Ile Leu Arg Asp
    450                 455                 460

Gly Leu Thr Ala Thr Glu Leu Glu His Arg Leu Ala Gly Asn Ala Ala
465                 470                 475                 480

Ser Val Ala Arg Ser Gly Gly Gly Gly Gly Gly Pro Ser Lys Pro Thr
                485                 490                 495

Ala Gln Lys Thr Ser Pro Ala Glu Ala Lys Pro Met Ser Ile Phe Tyr
            500                 505                 510

Gly Ser Asn Thr Gly Thr Cys Glu Ser Leu Ala Gln Arg Leu Ala Thr
        515                 520                 525

Asp Ala Ala Ser His Gly Tyr Ala Ala Ala Ala Val Glu Pro Leu Asp
    530                 535                 540

Thr Ala Thr Glu Lys Leu Pro Thr Asp Arg Pro Val Val Ile Ile Thr
545                 550                 555                 560

Ala Ser Phe Glu Gly Gln Pro Pro Asp Asn Ala Ala Lys Phe Cys Gly
                565                 570                 575

Trp Leu Lys Asn Leu Glu Gly Asp Glu Leu Lys Asn Val Ser Tyr Ala
            580                 585                 590

Val Phe Gly Cys Gly His His Asp Trp Ser Gln Thr Phe His Arg Ile
        595                 600                 605

Pro Lys Leu Val His Gln Thr Met Lys Ala His Gly Ala Ser Pro Ile
    610                 615                 620

Cys Asp Glu Gly Leu Thr Asp Val Ala Glu Gly Asn Met Phe Thr Asp
625                 630                 635                 640

Phe Glu Gln Trp Glu Asp Asp Val Phe Trp Pro Ala Val Arg Ala Arg
                645                 650                 655

Tyr Gly Ala Ala Gly Ala Val Ala Glu Thr Glu Asp Ala Pro Gly Ser
            660                 665                 670

Asp Gly Leu Asn Ile His Phe Ser Ser Pro Arg Ser Ser Thr Leu Arg
        675                 680                 685

Gln Asp Val Arg Glu Ala Thr Val Val Gly Glu Ala Leu Leu Thr Ala
    690                 695                 700

Pro Asp Ala Pro Pro Lys Lys His Ile Glu Val Gln Leu Pro Asp Gly
705                 710                 715                 720

Ala Thr Tyr Lys Val Gly Asp Tyr Leu Ala Val Leu Pro Val Asn Ser
                725                 730                 735
```

```
Lys Glu Ser Ile Gly Arg Val Met Arg Lys Phe Gln Leu Ser Trp Asp
            740                 745                 750

Ser His Val Thr Ile Ala Ser Asp Arg Trp Thr Ala Leu Pro Thr Gly
        755                 760                 765

Thr Pro Val Pro Ala Tyr Asp Val Leu Gly Ser Tyr Val Glu Leu Ser
    770                 775                 780

Gln Pro Ala Thr Lys Arg Gly Ile Leu Arg Leu Ala Asp Ala Ala Glu
785                 790                 795                 800

Asp Glu Ala Thr Lys Ala Glu Leu Gln Lys Leu Ala Gly Asp Leu Tyr
                805                 810                 815

Thr Ser Glu Ile Ser Leu Lys Arg Ala Ser Val Leu Asp Leu Leu Asp
            820                 825                 830

Arg Phe Pro Ser Ile Ser Leu Pro Phe Gly Thr Phe Leu Ser Leu Leu
        835                 840                 845

Pro Pro Ile Arg Pro Arg Gln Tyr Ser Ile Ser Ser Ser Pro Leu Asn
    850                 855                 860

Asp Pro Ser Arg Ala Thr Leu Thr Tyr Ser Leu Leu Asp Ser Pro Ser
865                 870                 875                 880

Leu Ala Asn Pro Ser Arg Arg Phe Val Gly Val Ala Thr Ser Tyr Leu
                885                 890                 895

Ser Ser Leu Val Arg Gly Asp Lys Leu Leu Val Ser Val Arg Pro Thr
            900                 905                 910

His Thr Ala Phe Arg Leu Pro Asp Glu Asp Lys Met Gly Glu Thr Ala
        915                 920                 925

Ile Ile Cys Val Gly Ala Gly Ser Gly Leu Ala Pro Phe Arg Gly Phe
    930                 935                 940

Ile Gln Glu Arg Ala Ala Leu Leu Ala Lys Gly Thr Gln Leu Ala Ala
945                 950                 955                 960

Ala Leu Leu Phe Tyr Gly Cys Arg Ser Pro Glu Lys Asp Asp Leu Tyr
                965                 970                 975

Arg Asp Glu Phe Asp Lys Trp Gln Glu Ser Gly Ala Val Asp Val Arg
            980                 985                 990

Arg Ala Phe Ser Arg Val Asp Ser  Asp Asp Thr Glu Ala  Arg Gly Cys
        995                 1000                1005

Arg His  Val Gln Asp Arg Leu  Trp His Asp Arg Glu  Glu Val Lys
    1010                1015                1020

Ala Leu  Trp Asp Arg Gly Ala  Arg Val Tyr Val Cys  Gly Ser Arg
    1025                1030                1035

Gln Val  Gly Glu Gly Val Lys  Thr Ala Met Gly Arg  Ile Val Leu
    1040                1045                1050

Gly Glu  Glu Asp Ala Glu Asp  Ala Ile Ser Lys Trp  Tyr Glu Thr
    1055                1060                1065

Val Arg  Asn Asp Arg Tyr Ala  Thr Asp Val Phe Asp
    1070                1075                1080


<210> SEQ ID NO 4
<211> LENGTH: 416
<212> TYPE: PRT
<213> ORGANISM: Escherichia coli

<400> SEQUENCE: 4

Met Glu Ser Lys Val Val Val Pro Ala Gln Gly Lys Lys Ile Thr Leu
1               5                   10                  15

Gln Asn Gly Lys Leu Asn Val Pro Glu Asn Pro Ile Ile Pro Tyr Ile
            20                  25                  30
```

-continued

```
Glu Gly Asp Gly Ile Gly Val Asp Val Thr Pro Ala Met Leu Lys Val
        35                  40                  45

Val Asp Ala Ala Val Glu Lys Ala Tyr Lys Gly Glu Arg Lys Ile Ser
    50                  55                  60

Trp Met Glu Ile Tyr Thr Gly Glu Lys Ser Thr Gln Val Tyr Gly Gln
65                  70                  75                  80

Asp Val Trp Leu Pro Ala Glu Thr Leu Asp Leu Ile Arg Glu Tyr Arg
                85                  90                  95

Val Ala Ile Lys Gly Pro Leu Thr Thr Pro Val Gly Gly Gly Ile Arg
            100                 105                 110

Ser Leu Asn Val Ala Leu Arg Gln Glu Leu Asp Leu Tyr Ile Cys Leu
        115                 120                 125

Arg Pro Val Arg Tyr Tyr Gln Gly Thr Pro Ser Pro Val Lys His Pro
    130                 135                 140

Glu Leu Thr Asp Met Val Ile Phe Arg Glu Asn Ser Glu Asp Ile Tyr
145                 150                 155                 160

Ala Gly Ile Glu Trp Lys Ala Asp Ser Ala Asp Ala Glu Lys Val Ile
                165                 170                 175

Lys Phe Leu Arg Glu Glu Met Gly Val Lys Lys Ile Arg Phe Pro Glu
            180                 185                 190

His Cys Gly Ile Gly Ile Lys Pro Cys Ser Glu Glu Gly Thr Lys Arg
        195                 200                 205

Leu Val Arg Ala Ala Ile Glu Tyr Ala Ile Ala Asn Asp Arg Asp Ser
    210                 215                 220

Val Thr Leu Val His Lys Gly Asn Ile Met Lys Phe Thr Glu Gly Ala
225                 230                 235                 240

Phe Lys Asp Trp Gly Tyr Gln Leu Ala Arg Glu Glu Phe Gly Gly Glu
                245                 250                 255

Leu Ile Asp Gly Gly Pro Trp Leu Lys Val Lys Asn Pro Asn Thr Gly
            260                 265                 270

Lys Glu Ile Val Ile Lys Asp Val Ile Ala Asp Ala Phe Leu Gln Gln
        275                 280                 285

Ile Leu Leu Arg Pro Ala Glu Tyr Asp Val Ile Ala Cys Met Asn Leu
    290                 295                 300

Asn Gly Asp Tyr Ile Ser Asp Ala Leu Ala Ala Gln Val Gly Gly Ile
305                 310                 315                 320

Gly Ile Ala Pro Gly Ala Asn Ile Gly Asp Glu Cys Ala Leu Phe Glu
                325                 330                 335

Ala Thr His Gly Thr Ala Pro Lys Tyr Ala Gly Gln Asp Lys Val Asn
            340                 345                 350

Pro Gly Ser Ile Ile Leu Ser Ala Glu Met Met Leu Arg His Met Gly
        355                 360                 365

Trp Thr Glu Ala Ala Asp Leu Ile Val Lys Gly Met Glu Gly Ala Ile
    370                 375                 380

Asn Ala Lys Thr Val Thr Tyr Asp Phe Glu Arg Leu Met Asp Gly Ala
385                 390                 395                 400

Lys Leu Leu Lys Cys Ser Glu Phe Gly Asp Ala Ile Ile Glu Asn Met
                405                 410                 415
```

<210> SEQ ID NO 5
<211> LENGTH: 3573
<212> TYPE: DNA
<213> ORGANISM: Unknown
<220> FEATURE:

<223> OTHER INFORMATION: Umbelopsis isabellina

<400> SEQUENCE: 5

```
atgagcacca ccaccctgat tgtggccatt aagggtaccg ataatgttga acgtgatggc     60
gcaattgttc gtctggatgc cggcgccagt atggaaaccc tgcgtccgcg cattgcagaa    120
aaactggcca ttagcagtgg cattgaagat ctgattctgg aagatgcaaa tggtgacaat    180
ctgaccacca ttgatcaggt tcgtaaacag cagaccgttt ttgttaatct ggaagatcag    240
attaagctgc cggcagttcc ggcccatacc ctgccgtatt ttggtaatct gtatcagctg    300
ctgccggata tgctggccgg ttggcgcaaa ctgtttgatg aatatggtcc ggttgttaaa    360
gtgaatctgc tgggcaatga aattattggt accaatgatc cggccgtggc cgaactgtgg    420
gttaaagaaa gcgaatattt taccaaaaag atctacggtg gcctgcagga agttaaaagt    480
tttggcggcc agggtctgtt taccaccgat agcgatgata tggattggaa actggcacat    540
aaactgctga tgccggcatt ttcaccgcgc gccattaagg tttatcagca tgaaatgagc    600
gtgattggtc tgcagaccat taaggttttt gaacagtata gcccggatga agaagtggaa    660
attctgcatt ggaccaccaa tctgaccttt gaaaccattg gcaaagttgg ttttggctat    720
gattttcatc tgctggatga tcgttatggc gaaaatcatc cgtttattga agcaatgggt    780
tattgcatga aacagagctt tgcccgtggc acccagagca aactgattaa gtatctgccg    840
attgaagcca atcgtcgcta tgatcgcagt ctgaatctga tgcatagcat tgttgatgaa    900
gttattaccc agcgtaaaag ccatccgcat gcaagcgaag ataataagga tctgctggat    960
tttatgctga ccgcacgtga tgaaaataat ctgggcctga gcgatgaaaa tattcgcgat   1020
caggttatta cctttctgat tgccggccat gaaaccacca gcaataccct ggcatggacc   1080
ctgtatgaac tgagtcgcca tccggaaatt gaacagaaaa ttctgcagga agtggtgaat   1140
ctgggcatta ccaccgattc actgccgacc agcgaacaga gcagtagcat gaaatatacc   1200
tatcaggtgc tgaaagaaac cctgcgcatg tatagtccgc tgcgtgcact ggcaaaatat   1260
tgcaaaaaag atattgtggt gccgggcggc tatcagatta aggcaggcga tcgtgtggcc   1320
gttcagctga atagcctgca ttataatgaa aaagtttacc cgaatccgac ccagtatgat   1380
ccgagtcgct ggaccccgga agaagaacag aaacgcagtc gctttgcctg gctgccgttt   1440
agcaccggcc cgcgtagctg cattggtatg gcactggccc tgcaggaagc aaaaaccatt   1500
ctggcaatga ttctgctgaa atttcgcttt gtttatgatg gtccgccgat tggttatgat   1560
ccgaaaagcc cgaccattcg tccgctgaat ctgatgatga aattctgcc gcgtgataaa    1620
ctgccgagcc cgaccgccga taataagctg accccggttg gcagtccgaa tattggtaaa   1680
gcccagatgg caatgccgac cgcagccacc aatgttggta ccgccgaact gccgccggtt   1740
ttctttctgt atggtaccca gaccggtacc gcccaggatt atgcaagtca gctggcaagc   1800
caggccaaaa gttttggttt taaagatatt accctgtgtg aaatggataa atgggaagtg   1860
ctgcagagcg gcaaatatac cggtgccaaa gaagaaaaag atacccgtgc cctggttgtt   1920
atttgtaccg caacctataa tggcagcccg ccggatagtg cagaaaattt tgataaattc   1980
attaccgaca ccagcaaaga taatgatctg ccgctgaaag gcctgctgta taccgtgttt   2040
ggcctgggca atcgtaattg gcgcacctat cagcagtttc cgattaagtg cgatgcccgt   2100
ctggatgaac tgggtggtga acgcttttat gatctgggca gcggcaatgc cgataaagat   2160
atggatggtg aatttcatga ttggtgcgcc catttttgga cccataccct gacctattat   2220
ggcattgcaa cccatgaagg tagtgcaagt ctggtgccgg gccagaaaac caccgaagat   2280
```

```
ccgaccagcg gtctggaaat tcgttttatt ccgccgagcg aaagcgaagc ctgggataaa   2340

gccgataaaa atgttaatgg tgactataat gcggaaattc aggtgaatcg cgaactgcag   2400

aatattgaac gtagtaaacg tagcacccgc catattgaaa ttgatattag taaactgcag   2460

agcccggata ccgataaaca tcgttatctg accggtgacc atctggaagt gtatccggaa   2520

aatgccgata atgtggtgga aagcattgcc ctgggctttg gtctgattct ggatagtgtg   2580

tttgaaatta ccagcgtgga taaaagtacc gtgagtagtc gtagcctggc agccagtatt   2640

accggcccgt gtaccgttcg taatgccctg aaatattatg ccgatatata tagtgccccg   2700

agccgttatc tgctggcctt tttcgcagca cgcctgcagg atacccatcc ggatgttgcc   2760

gcaagtttta gcgatgtgat tattccgggt gaaaatggcc agaaagccta taatgaattc   2820

attcagaaat accgtaacct gctggatctg cagcgcggct ttccgctgaa agaactggat   2880

ctgaaagaat ttctgtgcgc agttagcgtt atgcagccgc gccgttatag cattgccagc   2940

agcccgctga aagcagaaga taccgcatat ctggcagttg gtgtggtgga tgatgtgttt   3000

gcaaatcgtc attattatgg cctggccagt ggctatctgg cccgcagcca gccgccgaca   3060

ccgattcgtg cacgtattaa gagtagcaaa agtacctttg gcctgccgga aaatccggaa   3120

accccgatta ttatgattgg tgccggtacc ggtattagtc cgtttatggg ctttatgcag   3180

gaacgcgaaa tgctgaaaag caaagcagaa gcccatctgt tttcggctg ccgccatccg   3240

gatgaagatt ttatctatcg tagcgttttt gaaggctatg aaaaaagcgg cgttattacc   3300

aaactgtatc cggcctttag ccgtctgggt gaagataatc cgcgcaaata tgttcagcat   3360

cagctgatgg caaatgccgg caaaatttgg accctgctga ccaatggcgc aaatgtgtat   3420

gtttgcggca gtggcccgat gagccgcgat gtgcgtcgta gctttgaact gatggcaaaa   3480

agttttggag gcgccaaaac cgatgatgaa gcatgcgaaa aactgctgga attcatgagc   3540

gcaggtcgtt ataatgaaga tgtgtggggt taa                                3573
```

<210> SEQ ID NO 6
<211> LENGTH: 1190
<212> TYPE: PRT
<213> ORGANISM: Unknown
<220> FEATURE:
<223> OTHER INFORMATION: Umbelopsis isabellina

<400> SEQUENCE: 6

```
Met Ser Thr Thr Thr Leu Ile Val Ala Ile Lys Gly Thr Asp Asn Val
1               5                   10                  15

Glu Arg Asp Gly Ala Ile Val Arg Leu Asp Ala Gly Ala Ser Met Glu
            20                  25                  30

Thr Leu Arg Pro Arg Ile Ala Glu Lys Leu Ala Ile Ser Ser Gly Ile
        35                  40                  45

Glu Asp Leu Ile Leu Glu Asp Ala Asn Gly Asp Asn Leu Thr Thr Ile
    50                  55                  60

Asp Gln Val Arg Lys Gln Gln Thr Val Phe Val Asn Leu Glu Asp Gln
65                  70                  75                  80

Ile Lys Leu Pro Ala Val Pro Ala His Thr Leu Pro Tyr Phe Gly Asn
                85                  90                  95

Leu Tyr Gln Leu Leu Pro Asp Met Leu Ala Gly Trp Arg Lys Leu Phe
            100                 105                 110

Asp Glu Tyr Gly Pro Val Val Lys Val Asn Leu Leu Gly Asn Glu Ile
        115                 120                 125
```

```
Ile Gly Thr Asn Asp Pro Ala Val Ala Glu Leu Trp Val Lys Glu Ser
    130                 135                 140

Glu Tyr Phe Thr Lys Lys Ile Tyr Gly Gly Leu Gln Glu Val Lys Ser
145                 150                 155                 160

Phe Gly Gly Gln Gly Leu Phe Thr Thr Asp Ser Asp Asp Met Asp Trp
                165                 170                 175

Lys Leu Ala His Lys Leu Leu Met Pro Ala Phe Ser Pro Arg Ala Ile
            180                 185                 190

Lys Val Tyr Gln His Glu Met Ser Val Ile Gly Leu Gln Thr Ile Lys
        195                 200                 205

Val Phe Glu Gln Tyr Ser Pro Asp Glu Glu Val Glu Ile Leu His Trp
    210                 215                 220

Thr Thr Asn Leu Thr Phe Glu Thr Ile Gly Lys Val Gly Phe Gly Tyr
225                 230                 235                 240

Asp Phe His Leu Leu Asp Asp Arg Tyr Gly Glu Asn His Pro Phe Ile
                245                 250                 255

Glu Ala Met Gly Tyr Cys Met Lys Gln Ser Phe Ala Arg Gly Thr Gln
            260                 265                 270

Ser Lys Leu Ile Lys Tyr Leu Pro Ile Glu Ala Asn Arg Arg Tyr Asp
        275                 280                 285

Arg Ser Leu Asn Leu Met His Ser Ile Val Asp Glu Val Ile Thr Gln
    290                 295                 300

Arg Lys Ser His Pro His Ala Ser Glu Asp Asn Lys Asp Leu Leu Asp
305                 310                 315                 320

Phe Met Leu Thr Ala Arg Asp Glu Asn Asn Leu Gly Leu Ser Asp Glu
                325                 330                 335

Asn Ile Arg Asp Gln Val Ile Thr Phe Leu Ile Ala Gly His Glu Thr
            340                 345                 350

Thr Ser Asn Thr Leu Ala Trp Thr Leu Tyr Glu Leu Ser Arg His Pro
        355                 360                 365

Glu Ile Glu Gln Lys Ile Leu Gln Glu Val Val Asn Leu Gly Ile Thr
    370                 375                 380

Thr Asp Ser Leu Pro Thr Ser Glu Gln Ser Ser Ser Met Lys Tyr Thr
385                 390                 395                 400

Tyr Gln Val Leu Lys Glu Thr Leu Arg Met Tyr Ser Pro Leu Arg Ala
                405                 410                 415

Leu Ala Lys Tyr Cys Lys Lys Asp Ile Val Val Pro Gly Gly Tyr Gln
            420                 425                 430

Ile Lys Ala Gly Asp Arg Val Ala Val Gln Leu Asn Ser Leu His Tyr
        435                 440                 445

Asn Glu Lys Val Tyr Pro Asn Pro Thr Gln Tyr Asp Pro Ser Arg Trp
    450                 455                 460

Thr Pro Glu Glu Glu Gln Lys Arg Ser Arg Phe Ala Trp Leu Pro Phe
465                 470                 475                 480

Ser Thr Gly Pro Arg Ser Cys Ile Gly Met Ala Leu Ala Leu Gln Glu
                485                 490                 495

Ala Lys Thr Ile Leu Ala Met Ile Leu Leu Lys Phe Arg Phe Val Tyr
            500                 505                 510

Asp Gly Pro Pro Ile Gly Tyr Asp Pro Lys Ser Pro Thr Ile Arg Pro
        515                 520                 525

Leu Asn Leu Met Met Lys Ile Leu Pro Arg Asp Lys Leu Pro Ser Pro
    530                 535                 540

Thr Ala Asp Asn Lys Leu Thr Pro Val Gly Ser Pro Asn Ile Gly Lys
```

```
545                 550                 555                 560

Ala Gln Met Ala Met Pro Thr Ala Ala Thr Asn Val Gly Thr Ala Glu
                565                 570                 575

Leu Pro Pro Val Phe Phe Leu Tyr Gly Thr Gln Thr Gly Thr Ala Gln
            580                 585                 590

Asp Tyr Ala Ser Gln Leu Ala Ser Gln Ala Lys Ser Phe Gly Phe Lys
        595                 600                 605

Asp Ile Thr Leu Cys Glu Met Asp Lys Trp Glu Val Leu Gln Ser Gly
    610                 615                 620

Lys Tyr Thr Gly Ala Lys Glu Glu Lys Asp Thr Arg Ala Leu Val Val
625                 630                 635                 640

Ile Cys Thr Ala Thr Tyr Asn Gly Ser Pro Pro Asp Ser Ala Glu Asn
                645                 650                 655

Phe Asp Lys Phe Ile Thr Asp Thr Ser Lys Asp Asn Asp Leu Pro Leu
            660                 665                 670

Lys Gly Leu Leu Tyr Thr Val Phe Gly Leu Gly Asn Arg Asn Trp Arg
        675                 680                 685

Thr Tyr Gln Gln Phe Pro Ile Lys Cys Asp Ala Arg Leu Asp Glu Leu
    690                 695                 700

Gly Gly Glu Arg Phe Tyr Asp Leu Gly Ser Gly Asn Ala Asp Lys Asp
705                 710                 715                 720

Met Asp Gly Glu Phe His Asp Trp Cys Ala His Phe Trp Thr His Thr
                725                 730                 735

Leu Thr Tyr Tyr Gly Ile Ala Thr His Glu Gly Ser Ala Ser Leu Val
            740                 745                 750

Pro Gly Gln Lys Thr Thr Glu Asp Pro Thr Ser Gly Leu Glu Ile Arg
        755                 760                 765

Phe Ile Pro Pro Ser Glu Ser Glu Ala Trp Asp Lys Ala Asp Lys Asn
    770                 775                 780

Val Asn Gly Asp Tyr Asn Ala Glu Ile Gln Val Asn Arg Glu Leu Gln
785                 790                 795                 800

Asn Ile Glu Arg Ser Lys Arg Ser Thr Arg His Ile Glu Ile Asp Ile
                805                 810                 815

Ser Lys Leu Gln Ser Pro Asp Thr Asp Lys His Arg Tyr Leu Thr Gly
            820                 825                 830

Asp His Leu Glu Val Tyr Pro Glu Asn Ala Asp Asn Val Val Glu Ser
        835                 840                 845

Ile Ala Leu Gly Phe Gly Leu Ile Leu Asp Ser Val Phe Glu Ile Thr
    850                 855                 860

Ser Val Asp Lys Ser Thr Val Ser Ser Arg Ser Leu Ala Ala Ser Ile
865                 870                 875                 880

Thr Gly Pro Cys Thr Val Arg Asn Ala Leu Lys Tyr Tyr Ala Asp Ile
                885                 890                 895

Tyr Ser Ala Pro Ser Arg Tyr Leu Leu Ala Phe Phe Ala Ala Arg Leu
            900                 905                 910

Gln Asp Thr His Pro Asp Val Ala Ala Ser Phe Ser Asp Val Ile Ile
        915                 920                 925

Pro Gly Glu Asn Gly Gln Lys Ala Tyr Asn Glu Phe Ile Gln Lys Tyr
    930                 935                 940

Arg Asn Leu Leu Asp Leu Gln Arg Gly Phe Pro Leu Lys Glu Leu Asp
945                 950                 955                 960

Leu Lys Glu Phe Leu Cys Ala Val Ser Val Met Gln Pro Arg Arg Tyr
                965                 970                 975
```

```
Ser Ile Ala Ser Ser Pro Leu Lys Ala Glu Asp Thr Ala Tyr Leu Ala
            980                 985                 990

Val Gly Val Val Asp Asp Val Phe  Ala Asn Arg His Tyr  Tyr Gly Leu
        995                 1000                 1005

Ala Ser  Gly Tyr Leu Ala Arg  Ser Gln Pro Pro Thr  Pro Ile Arg
    1010                 1015                 1020

Ala Arg  Ile Lys Ser Ser Lys  Ser Thr Phe Gly Leu  Pro Glu Asn
    1025                 1030                 1035

Pro Glu  Thr Pro Ile Ile Met  Ile Gly Ala Gly Thr  Gly Ile Ser
    1040                 1045                 1050

Pro Phe  Met Gly Phe Met Gln  Glu Arg Glu Met Leu  Lys Ser Lys
    1055                 1060                 1065

Ala Glu  Ala His Leu Phe Phe  Gly Cys Arg His Pro  Asp Glu Asp
    1070                 1075                 1080

Phe Ile  Tyr Arg Ser Val Phe  Glu Gly Tyr Glu Lys  Ser Gly Val
    1085                 1090                 1095

Ile Thr  Lys Leu Tyr Pro Ala  Phe Ser Arg Leu Gly  Glu Asp Asn
    1100                 1105                 1110

Pro Arg  Lys Tyr Val Gln His  Gln Leu Met Ala Asn  Ala Gly Lys
    1115                 1120                 1125

Ile Trp  Thr Leu Leu Thr Asn  Gly Ala Asn Val Tyr  Val Cys Gly
    1130                 1135                 1140

Ser Gly  Pro Met Ser Arg Asp  Val Arg Arg Ser Phe  Glu Leu Met
    1145                 1150                 1155

Ala Lys  Ser Phe Gly Gly Ala  Lys Thr Asp Asp Glu  Ala Cys Glu
    1160                 1165                 1170

Lys Leu  Leu Glu Phe Met Ser  Ala Gly Arg Tyr Asn  Glu Asp Val
    1175                 1180                 1185

Trp Gly
    1190


<210> SEQ ID NO 7
<211> LENGTH: 30
<212> TYPE: DNA
<213> ORGANISM: Artificial Sequence
<220> FEATURE:
<223> OTHER INFORMATION: Primer

<400> SEQUENCE: 7

ggaattccat atggaaagta aagtagttgt                                      30


<210> SEQ ID NO 8
<211> LENGTH: 32
<212> TYPE: DNA
<213> ORGANISM: Artificial Sequence
<220> FEATURE:
<223> OTHER INFORMATION: Primer

<400> SEQUENCE: 8

ccgctcgagt tacatgtttt cgatgatcgc gt                                   32
```

BIOSYNTHETIC PRODUCTION OF GAMMA- AND DELTA-LACTONES USING CYTOCHROME P450 ENZYMES HAVING SUBTERMINAL HYDROXYLASE ACTIVITY

CROSS-REFERENCE TO RELATED APPLICATIONS

This Application is a Continuation of International Patent Application No. PCT/US2020/024071, filed Mar. 21, 2020, entitled "BIOSYNTHETIC PRODUCTION OF GAMMA- AND DELTA-LACTONES USING CYTOCHROME P450 ENZYMES HAVING SUBTERMINAL HYDROXYLASE ACTIVITY", which claims the priority of the U.S. Provisional Application Ser. No. 62/821,894, filed on Mar. 21, 2019, the entire contents each of which are incorporated herein by reference.

REFERENCE TO AN ELECTRONIC SEQUENCE LISTING

The contents of the electronic sequence listing (C149770067US01-SEQ-ZJG.xml; Size: 38,878 bytes; and Date of Creation: Sep. 21, 2021) is herein incorporated by reference in its entirety.

FIELD OF THE INVENTION

The field of the invention relates to methods and processes for producing gamma- and delta-lactones via modified microbial cultures. More specifically, the present disclosure relates to the production of gamma- and delta-lactones having 5-8 carbon atoms from corresponding fatty acid substrates via enzymatic conversion.

BACKGROUND OF THE INVENTION

There exists a universal desire for foods, fragrances and cosmetics that have pleasant tastes and odors. In many cases, these traits of pleasant smells and tastes are provided through various lactone compounds, including various gamma- and delta-lactones, that possess desirable aroma and flavor characteristics. Current demand for lactone compounds is mainly addressed through either chemical synthesis or extraction processes from plants. Plant extraction-based production has significant disadvantages, such as weather effects on the strength and abundance of the compounds of interest, risk of plant diseases and/or poor harvest, stability of the compound, environmental impact of increased production and trade restrictions. Industrial production can cause environmental damage, may use dangerous precursors and itself may be subject to increased cost due to cost of key substrates.

Accordingly, there is a need in the art for novel methods to produce gamma- and delta-lactones economically and reliably without the limitations posed by plant extraction and chemical synthesis.

SUMMARY OF THE INVENTION

According to the current invention, lactones may be reliably produced at high yield by gene modification and fermentation technology using microorganisms such as bacteria and/or yeasts. These microorganisms are able to synthesize lactones de novo or by biotransformation of fatty acids to provide commercially significant yields. Hence, new production methods are provided herein to reduce costs of gamma- and delta-lactone production and lessen the environmental impact of large-scale cultivation and processing of natural sources from which these lactone compounds can be extracted.

More specifically, the present disclosure encompasses methods and compositions for making lactones by microbial fermentation, wherein the microbial fermentation comprises a cellular system expressing a heterologous cytochrome P450 (CYP450) protein.

The present disclosure is based, in part, on the finding that certain CYP450 proteins and functional variants thereof have hydroxylase activity at specific subterminal carbon atom positions. In particular, certain CYP450 proteins have been identified to cause hydroxylation of straight chain fatty acids at the first (ω-1), second (ω-2), and/or third (ω-3) carbon atoms adjacent to the terminal (ω) carbon atom. By overexpressing these CYP450 proteins in a modified microbial system and feeding straight chain fatty acids as substrates to the said modified microbial system, ω-1, ω-2, and ω-3 hydroxy fatty acids are produced which then can be converted efficiently into various gamma- and delta-lactones at high titers. The present disclosure, therefore, provides economical and reliable methods for producing gamma- and delta-lactones from straight chain fatty acids without the disadvantages associated with chemical synthesis or plant extraction as described above.

Accordingly, one aspect of the present disclosure provides a method for making lactones comprising (a) incubating a cellular system expressing a heterologous CYP450 protein with a medium comprising a straight chain fatty acid to produce a subterminal hydroxy fatty acid, and incubating the resulting subterminal hydroxy fatty acid with a cell culture followed by acid treatment to produce one or more gamma- and delta-lactones.

In some embodiments, the CYP450 protein comprises an amino acid sequence that is at least 90% (e.g., at least 90%, at least 91%, at least 92%, at least 93%, at least 94%) identical to the amino acid sequence of CYP450 from *Myceliophthora* thermophile. In some embodiments, the CYP450 protein comprises an amino acid sequence that is at least 95% (e.g., at least 95%, at least 96%, at least 97%, at least 98%, at least 99%) identical to the amino acid sequence of CYP450 from *Myceliophthora* thermophile. In some embodiments, the CYP450 protein from *Myceliophthora* thermophile comprises the amino acid sequence of SEQ ID NO: 3.

In some embodiments, the CYP450 protein comprises an amino acid sequence that is at least 90% (e.g., at least 90%, at least 91%, at least 92%, at least 93%, at least 94%) identical to the amino acid sequence of CYP450 from *Umbelopsis isabellina*. In some embodiments, the CYP450 protein comprises an amino acid sequence that is at least 95% (e.g., at least 95%, at least 96%, at least 97%, at least 98%, at least 99%) identical to the amino acid sequence of CYP450 from *Umbelopsis isabellina*. In some embodiments, the CYP450 protein from *Umbelopsis isabellina* comprises the amino acid sequence of SEQ ID NO: 6.

Any methods described herein may further comprise expressing an isocitrate dehydrogenase (Icd) protein (e.g., a heterologous Icd) in the cellular system. In some embodiments, the Icd protein comprises an amino acid sequence that is at least 90% (e.g., at least 90%, at least 91%, at least 92%, at least 93%, at least 94%) identical to the amino acid sequence of Icd from *E. coli*. In some embodiments, the Icd protein comprises an amino acid sequence that is at least 95% (e.g., at least 95%, at least 96%, at least 97%, at least 98%, at least 99%) identical to the amino acid sequence of Icd from *E. coli*. In some embodiments, the Icd protein from *E. coli* comprises the amino acid sequence of SEQ ID NO: 4.

In some embodiments, the straight chain fatty acid comprises 5 carbon atoms to 40 carbon atoms. In preferred embodiments, the straight chain fatty acid comprises 7 carbon atoms to 20 carbon atoms. In some embodiments, the fatty acid is selected from lauric acid, tridecylic acid, or a combination thereof. In some embodiments, the subterminal hydroxy fatty acid comprises hydroxylated lauric acid, hydroxylated tridecylic acid, or a combination thereof. In some embodiments, the subterminal hydroxy fatty acid comprises a hydroxyl group at a position selected from the group consisting of ω-1, ω-2, and ω-3.

In some embodiments, the cellular system can comprise growing cells. In some embodiments, the cellular system can comprise lyophilized cells. In some embodiments the cellular system can comprise bacterial cells, yeast cells, plant cells that do not naturally produce the lactone of interest, algal cells, fungal cells, or combinations thereof, one or more of which have been transformed to overexpress the protein(s) described herein. In some embodiments, the cellular system can comprise bacteria and/or yeast cells selected from the group consisting of *Escherichia; Salmonella; Bacillus; Acinetobacter; Streptomyces; Corynebacterium; Methylosinus; Methylomonas; Rhodococcus; Pseudomonas; Rhodobacter; Synechocystis; Saccharomyces; Zygosaccharomyces; Kluyveromyces; Candida; Hansenula*; Debaryomyces; *Mucor; Pichia; Torulopsis; Aspergillus; Arthrobotrys*; Brevibacteria; *Microbacterium; Arthrobacter; Citrobacter; Klebsiella; Mucor; Pantoea; Corynebacterium*; and *Clostridium*.

In some embodiments, the lactones can comprise five carbons to eight carbons. In some embodiments, the lactones comprise one or more of δ-hexalactone, γ-hexalactone, and δ-octalactone. In some embodiments, the lactones comprise one or more of γ-valerolactone, δ-heptalactone, and γ-heptalactone.

In some embodiments, the straight chain fatty acid is lauric acid, the subterminal hydroxy fatty acid is hydroxy lauric acid, and the lactones comprises one or more of δ-hexalactone, γ-hexalactone, and δ-octalactone. In some embodiments, the straight chain fatty acid is tridecylic acid, the subterminal hydroxy fatty acid is hydroxy tridecylic acid, and the lactones comprise one or more of γ-valerolactone, δ-heptalactone, and γ-heptalactone. In some embodiments, the subterminal hydroxy fatty acid is isolated from the cellular system prior to treating it with cell culture.

Any methods described herein may further comprise isolating the lactones from the microbial cell culture or the acidic environment to provide a crude product. In some embodiments, the crude product obtained from such isolating step can include a lactone content that is at least 70% pure. In some embodiments, the method further comprises: i) purifying a crude product comprising the lactones; and, ii) removing solvents under vacuum to provide a concentrated product. In some embodiments, said crude product is purified by column chromatography. In some embodiments, said crude product is purified by acid-base extraction. In some embodiments, said crude product is purified by vacuum distillation. In some embodiments, the method further comprises purifying said lactones using a semi-preparative HPLC.

The disclosure further provides a fermentation product composition comprising a mixture of lactones, wherein the mixture of lactones comprises one or more gamma- and/or delta-lactones having 5 to 8 carbon atoms. The lactone content in the fermentation product composition can be at least 70% (e.g., at least 70%, at least 75%, at least 80%, at least 85%, at least 90%, at least 95%, at least 95%, at least 97%, at least 98%, at least 99% or 100%) of the crude mixture and then can be further purified out of the microbial cell culture.

One skilled in the art will recognize that the lactone composition(s) produced by the methods described herein can be further purified and mixed with other lactones, flavors, or scents to obtain a desired composition for use in a variety of consumer products or foods. For example, a lactone composition described herein can be included in food products (such as beverages, soft drinks, ice cream, dairy products, confectioneries, cereals, chewing gum, baked goods, etc.), dietary supplements, medical nutrition, as well as pharmaceutical products to give desired flavor or aromatic characteristics. In some embodiments, the disclosure provides a consumable product comprising a flavoring or scented amount of a lactone produced by any one of the methods above or described elsewhere herein for use in a specific flavoring context, formula or recipe. In some embodiments, the consumable product can be a food, beverage, perfume, or cosmetic product. In some embodiments, the composition can be selected from beverages, confectioneries, bakery products, cookies, and chewing gums. In certain embodiments, the composition can be a food, beverage, perfume, or cosmetic product having a favor or aroma profile designed to taste or smell like: peach, apricot, pear, maple, coconut, tropical, butterscotch, grenadine and/or date.

While the disclosure is susceptible to various modifications and alternative forms, specific embodiments thereof are shown by way of example in the drawing and will herein be described in detail. It should be understood, however, that the drawings and detailed description presented herein are not intended to limit the disclosure to the particular embodiment disclosed, but on the contrary, the intention is to cover all modifications, equivalents, and alternatives falling within the spirit and scope of the present disclosure as defined by the appended claims.

Other features and advantages of this invention will become apparent in the following detailed description of preferred embodiments of this invention, taken with reference to the accompanying drawings.

BRIEF DESCRIPTION OF THE DRAWINGS

The following drawings form part of the present specification and are included to further demonstrate certain aspects of the present disclosure, which can be better understood by reference to one or more of these drawings in combination with the detailed description of specific embodiments presented herein.

FIG. 4A is at the top. FIG. 4B is the second from top. FIG. 4C is in the middle. FIG. 4D is the fourth from top and FIG. 4E is at the bottom. Peaks are identified based on the retention times and mass spectra of the peaks compared with standards from Sigma. FIG. 4B and peak 1: γ-hexalactone (GC6); FIG. 4C and peak 2: δ-hexalactone (DC6); FIG. 4D and peak 3: phenethyl alcohol; and FIG. 4E and peak 4: δ-octalactone (DC8).

FIG. 6A is at the top. FIG. 6B is the second from top. FIG. 6C is the third from the top and FIG. 6D is at the bottom. FIG. 6B and peak 1: phenethyl alcohol; FIG. 6C and peak 2: γ-heptalactone (GC7); FIG. 6D and peak 3: δ-heptalactone (DC7).

FIG. 8A: *Candida boidinii* culture grown in MI2-C12-CSL medium. FIG. 8B: *Candida boidinii* culture grown in MI2-C13-CSL medium. Abbreviations in FIGS. 8A-8B have the following meaning: GC6: γ-hexalactone; DC7: δ-heptalactone (DC7); C12: lauric acid; C13: tridecanoic acid. Samples were taken 2 days after inoculation.

DESCRIPTION OF THE PREFERRED EMBODIMENT

Figure 1:
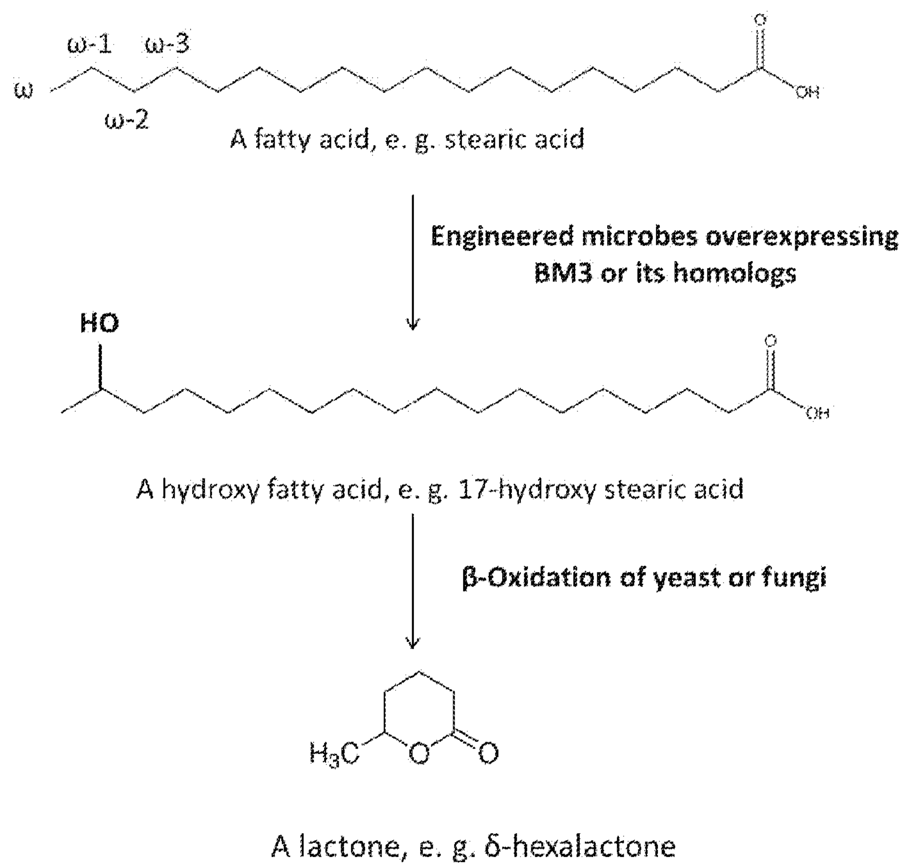
FIG. 1 shows a schematic diagram illustrating an embodiment of the biosynthetic pathway for producing gamma- and delta-lactones according to the present disclosure, in which a C18 fatty acid (stearic acid) is bioconverted into delta-hexalactone via a 2-step process involving the subterminal hydroxy fatty acid (17-hydroxy stearic acid) as an intermediate.

Lactones are industrially important flavor compounds that are widely found in foods, fruits, and beverages and are used in many fruity aromatic foods and cosmetics (see, e.g., Romero-Guido et al., 2011. Biochemistry of lactone formation in yeast and fungi and its utilization for the production of flavor and fragrance compounds. Appl. Microbiol. Biotechnol. 89:535-547). The present disclosure provides, in some embodiments, methods of making lactones from fatty acids. In some embodiments, the method comprises a first step, in which a cellular system expressing a heterologous cytochrome P450 (CYP450) protein converts fatty acids to hydroxy fatty acids. In some embodiments, the method comprises a second step, in which a microbial cell culture, e.g., a yeast cell culture, shorten the length of subterminal hydroxy fatty acids through a biochemical process called β-oxidation to appropriate length which upon cyclization yield appropriate lactones. Thus, the length of the subterminal hydroxy acids at the end of the second step of the process according to the present invention is shorter than the length of the subterminal hydroxy fatty acids obtained at the end of the first step of the process according to the present invention. In some embodiments, the second step further comprises an acidification step which induces the cyclization of the shortened subterminal hydroxy fatty acids to appropriate lactones. Methods provided herein further comprise isolating the lactones from the cell culture or the acidic environment.

Methods of Making Lactones

Methods described herein, in some embodiments, provide for the production of lactones from fatty acids. In some embodiments, methods of making lactones comprise (a) a step of incubating a cellular system expressing a heterologous cytochrome P450 (CYP450) protein with a medium comprising a straight chain fatty acid to produce a subterminal hydroxy fatty acid, (b) a step of incubating the subterminal hydroxyl fatty acid from step (a) with a microbial cell culture to shorten the length of the subterminal hydroxy acid to appropriate length and (c) a step of subjecting the shortened subterminal hydroxy acid from step (b) to cyclization in an acidic environment to obtain appropriate lactone.

In some embodiments, methods of making lactones comprise incubating cell pellets harvested from the cellular system expressing the heterologous CYP450 protein with a medium comprising fatty acids. In some embodiments, methods of making lactones comprise incubating resuspended cell pellets harvested from the cellular system with the medium comprising fatty acids.

Methods of making lactones described herein comprise incubating a cellular system expressing a heterologous CYP450 protein with a medium comprising fatty acids at any ratio. In some embodiments, methods of making lactones comprise incubating a cellular system comprising between 1 gram of cells per liter to 200 grams of cells per liter (1 g/L to 200 g/L) and a medium comprising between 1 gram of fatty acids per liter to 20 grams of fatty acids per liter (1 g/L to 20 g/L). In some embodiments, methods of making lactones comprise incubating a cellular system comprising 100 grams of cells per liter (100 g/L) and a medium comprising 3 grams of fatty acids per liter (3 g/L).

In some embodiments, methods of making lactones comprise incubating a cellular system with a medium comprising fatty acids for a suitable period sufficient for formation of hydroxy fatty acids. In some embodiments, methods of making lactones comprise contacting the hydroxy fatty acids with a cell culture for a suitable period sufficient for formation of lactones in the microbial cell culture. In some embodiments, methods of making lactones comprise isolating the hydroxy fatty acids from the cellular system prior to contact with the microbial cell culture. In some embodiments, methods of making lactones comprise incubating the hydroxy fatty acids in a medium with the microbial cell culture.

Methods of making lactones described herein encompass incubating a cellular system expressing a heterologous CYP450 protein with a medium comprising fatty acids for a specific period of time. In some embodiments, methods of making lactones comprise incubating a cellular system expressing a heterologous CYP450 protein with a medium comprising fatty acids for a period of time between 0.5 hour to 96 hours.

Methods of making lactones described herein encompass incubating a cellular system expressing a heterologous CYP450 protein with a medium comprising fatty acids at a specified temperature. In some embodiments, methods of making lactones comprise incubating a cellular system expressing a heterologous CYP450 protein with a medium comprising fatty acids at a temperature of 16° C. to 40° C.

Cytochrome P450

Cytochrome P450 (CYP450) proteins, generally, are enzymes that catalyze oxidation of substrates. CYP450 proteins are members of the hemeprotein superfamily, and contain heme as a cofactor. CYP450 enzymes have been identified in many organisms including, but not limited to, animals, plants, fungi, bacteria, archaea, and viruses. Any CYP450 protein that catalyzes subterminal hydroxylation of fatty acids may be used in methods described herein, or any functional variant or fragment thereof. Examples of CYP450 proteins that have been reported to have subterminal hydroxylase activity include, but are not limited to, CYP102A1 (or $P450_{BM3}$) from *Bacillus megaterium*, CYP450 protein from *Myceliophthora* thermophile (Uniprot #G2QDZ3), CYP450 from *Fusarium oxysporum*, CYP450 protein from *Umbelopsis isabellina*, CYP147G1 from *Mycobacterium marinum*, CYP109D1 from *Sorangium cellulosum*, CYP709C1 from Tritcum *aestivum*, CYP109B1 from *Bacillus subtilis*, CYP505D6 from *Phanerochaete chrysosporium*, or any functional variant or fragment thereof. In some embodiments, more than one CYP450 protein is used in a method described herein. In some embodiments, 2, 3, 4, or 5 different CYP450 proteins are used in a method described herein.

In some embodiments, the CYP450 protein comprises an amino acid sequence that is at least 75% identical to the amino acid sequence of CYP450 from *Myceliophthora* thermophile encoded by the nucleic acid sequence of SEQ ID NO: 1. In some embodiments, the CYP450 protein comprises an amino acid sequence that is at least 80%, at least 85%, at least 90%, at least 95%, at least 96%, at least 97%, at least 98%, or at least 99% identical to the amino acid sequence of CYP450 protein from *Myceliophthora* thermophile encoded by the nucleic acid sequence of SEQ ID NO: 1. In some embodiments, the CYP450 protein comprises an amino acid sequence encoded by nucleic acids in SEQ ID NO: 1.

In some embodiments, the CYP450 protein comprises an amino acid sequence that is at least 75% identical to the amino acid sequence of CYP450 from *Myceliophthora* thermophile provided in SEQ ID NO: 3. In some embodiments, the CYP450 protein comprises an amino acid sequence that is at least 80%, at least 85%, at least 90%, at least 95%, at least 96%, at least 97%, at least 98%, or at least 99% identical to the amino acid sequence of CYP450 protein from *Myceliophthora* thermophile provided in SEQ ID NO: 3. In some embodiments, the CYP450 protein comprises the amino acid sequence of SEQ ID NO: 3.

In some embodiments, the CYP450 protein comprises an amino acid sequence that is at least 75% identical to the amino acid sequence of CYP450 from *Umbelopsis isabellina* encoded by the nucleic acid sequence of SEQ ID NO: 5. In some embodiments, the CYP450 protein comprises an amino acid sequence that is at least 80%, at least 85%, at least 90%, at least 95%, at least 96%, at least 97%, at least 98%, or at least 99% identical to the amino acid sequence of CYP450 protein from *Umbelopsis isabellina* encoded by the nucleic acid sequence of SEQ ID NO: 5. In some embodiments, the CYP450 protein comprises an amino acid sequence encoded by nucleic acids in SEQ ID NO: 5.

In some embodiments, the CYP450 protein comprises an amino acid sequence that is at least 75% identical to the amino acid sequence of CYP450 from *Umbelopsis isabellina* provided in SEQ ID NO: 6. In some embodiments, the CYP450 protein comprises an amino acid sequence that is at least 80%, at least 85%, at least 90%, at least 95%, at least 96%, at least 97%, at least 98%, or at least 99% identical to the amino acid sequence of CYP450 protein from *Umbelopsis isabellina* provided in SEQ ID NO: 6. In some embodiments, the CYP450 protein comprises the amino acid sequence of SEQ ID NO: 6.

CYP450 proteins, in some embodiments, catalyze conversion of fatty acids to hydroxy fatty acids. In some embodiments, the CYP450 protein catalyzes formation of ω-1 to ω-3 hydroxy fatty acids. In some embodiments, the CYP450 protein catalyzes formation of ω-1 hydroxy fatty acids. In some embodiments, the CYP450 protein catalyzes formation of ω-2 hydroxy fatty acids. In some embodiments, the CYP450 protein catalyzes formation of ω-3 hydroxy fatty acids.

Isocitrate Dehydrogenase (Icd)

Isocitrate dehydrogenase (Icd) proteins, generally, are enzymes that catalyze oxidative decarboxylation of isocitrate. Icd proteins have been identified in many organisms including, but not limited to, animals, plants, fungi, bacteria, archaea, and viruses. Icd proteins, in some embodiments, convert $NAD^+$ to NADH or $NADP^+$ to NADPH. In some embodiments, NADH and/or NADPH generated by an Icd protein may be utilized by another enzyme (e.g., CYP450), thus promoting the activity of the other enzyme. Any Icd protein that catalyzes conversion of $NAD^+$ to NADH or $NADP^+$ to NADPH may be used in methods described herein, or any functional variant or fragment thereof. An example of an Icd protein includes, but is not limited to, Icd protein from *E. coli* (Uniprot #P08200). In some embodiments, more than one Icd protein is used in a method described herein. In some embodiments, 2, 3, 4, or 5 different Icd proteins are used in a method described herein.

In some embodiments, the Icd protein comprises an amino acid sequence that is at least 75% identical to the amino acid sequence of Icd from *E. coli* encoded by the nucleic acid sequence of SEQ ID NO: 2. In some embodiments, the Icd protein comprises an amino acid sequence that is at least 80%, at least 85%, at least 90%, at least 95%, at least 96%, at least 97%, at least 98%, or at least 99% identical to the amino acid sequence of Icd protein from *E. coli* encoded by the nucleic acid sequence of SEQ ID NO: 2. In some embodiments, the Icd protein comprises an amino acid sequence encoded by nucleic acids in SEQ ID NO: 2.

In some embodiments, the Icd protein comprises an amino acid sequence that is at least 75% identical to the amino acid sequence of Icd from *E. coli* provided in SEQ ID NO: 4. In some embodiments, the Icd protein comprises an amino acid sequence that is at least 80%, at least 85%, at least 90%, at least 95%, at least 96%, at least 97%, at least 98%, or at least 99% identical to the amino acid sequence of Icd protein from *E. coli* provided in SEQ ID NO: 4. In some embodiments, the Icd protein comprises the amino acid sequence of SEQ ID NO: 4.

Lactones

According to methods described herein, hydroxy fatty acids may be converted to lactones. According to the present disclosure, the methods provided herein convert subterminal hydroxy fatty acids into γ-lactones, δ-lactones, and combinations thereof. Examples of lactones include, but are not limited to, δ-hexalactone, γ-hexalactone, δ-octalactone, γ-valerolactone, δ-heptalactone, and γ-heptalactone.

In some embodiments, subterminal hydroxy lauric acid is converted to δ-hexalactone, γ-hexalactone, and/or δ-octalactone. In some embodiments, hydroxy tridecanoic acid is converted to γ-valerolactone, δ-heptalactone, and/or γ-heptalactone.

Lactones described herein, in some embodiments, comprise 5 carbons to 8 carbons. In some embodiments, the lactones comprise 5 carbons. In some embodiments, the lactones comprise 6 carbons. In some embodiments, the lactones comprise 7 carbons. In some embodiments, the lactones comprise 8 carbons.

Any lactones produced according to methods described herein may be isolated or purified from a cell culture using any method known in the art. In some embodiments, lactones are isolated or purified from the cell culture with chromatography. In some embodiments, lactones are isolated or purified from the cell culture with organic solvent. In some embodiments, the isolated or purified lactones can be incorporated into a product, e.g., a food, a beverage, a perfume or a cosmetic.

Fatty Acids

According to methods described herein, fatty acids may be converted to hydroxy fatty acids. Any fatty acid may be converted to its hydroxylated form in accordance with methods disclosed herein. Examples of fatty acids include, but are not limited to, pentanoic acid, hexanoic acid, heptanoic acid, octanoic acid, nonanoic acid, decanoic acid, undecanoic acid, dodecanoic acid, tridecanoic acid, tetradecanoic acid, pentadecanoic acid, hexadecanoic acid, heptadecanoic acid, octadecanoic acid, nonadecanoic acid, eicosanoic acid, heneicosanoic acid, docosanoic acid, tricosanoic acid, tetracosanoic acid, pentacosanoic acid, hexacosanoic acid, heptacosanoic acid, octacosanoic acid, nonacosanoic acid, triacontanoic acid, henatriacontanoic acid, dotriacontanoic acid, tritriacontanoic acid, tetratriacontanoic acid, pentatriacontanoic acid, hexatriacontanoic acid, heptatriacontanoic acid, octatriacontanoic acid, nonatriacontanoic acid, and tetracontanoic acid. Table 1 provides common names, structural formulas, and lipid numbers of exemplary fatty acids.

Fatty acids described herein, in some embodiments, comprise 5 carbons to 40 carbons. In some embodiments, the fatty acids comprise 5 carbons, 6 carbons, 7 carbons, 8 carbons, 9 carbons, 10 carbons, 11 carbons, 12 carbons, 13 carbons, 14 carbons, 15 carbons, 16 carbons, 17 carbons, 18 carbons, 19 carbons, 20 carbons, 21 carbons, 22 carbons, 23 carbons, 24 carbons, 25 carbons, 26 carbons, 27 carbons, 28 carbons, 29 carbons, 30 carbons, 31 carbons, 32 carbons, 33 carbons, 34 carbons, 35 carbons, 36 carbons, 37 carbons, 38 carbons, 39 carbons, 40 carbons, or more carbons.

Fatty acids described herein, in some embodiments, are provided in a medium. In some embodiments, the medium comprising fatty acids comprises a cell culture medium. In some embodiments, the medium comprising fatty acids comprises salts. Salts are combinations of anions and cations. Non-limiting examples of cations include lithium, sodium, potassium magnesium, calcium, and ammonium. Non-limiting examples of anions include acetate, chloride, sulfate, and phosphate. In some embodiments, the medium comprising fatty acids comprises isocitric acid trisodium salt.

In some embodiments, the medium comprising fatty acids comprises a buffer. Examples of buffers include, without limitation, phosphate buffer, Tris buffer, MOPS buffer, HEPES buffer, citrate buffer, acetate buffer, malate buffer, MES buffer, histidine buffer, PIPES buffer, bis-tris buffer, and ethanolamine buffer.

In some embodiments, the medium comprising fatty acids comprises a detergent. Non-limiting examples of detergents include polysorbate 20 (TWEEN® 20), polyoxyethylenesorbitan monopalmitate (TWEEN® 40), 4-(1,1,3,3-Tetramethylbutyl)phenyl-polyethylene glycol (TRITON™ X-100), sodium dodecyl sulfate (SDS), ethyl trimethylammonium bromide (ETMAB), lauryl trimethyl ammonium bromide (LTAB), and lauryl trimethylammonium chloride (LTAC).

A medium comprising fatty acids may comprise any concentration of fatty acids. In some embodiments, the medium comprising fatty acids comprises 0.5 g/L to 100 g/L fatty acids, e.g., 1 g/L to 10 g/L fatty acids. In some embodiments, the medium comprising fatty acids comprises 0.5 g/L, 1 g/L, 2 g/L, 3 g/L, 4 g/L, 5 g/L, 6 g/L, 7 g/L, 8 g/L, 9 g/L, 10 g/L, 20 g/L, 30 g/L, 40 g/L, 50 g/L, 60 g/L, 70 g/L, 80 g/L, 90 g/L or 100 g/L fatty acids.

Any fatty acid described herein may be hydroxylated according to methods described herein. In some embodiments, pentanoic acid is converted to hydroxylated pentanoic acid, hexanoic acid is converted to hydroxylated hexanoic acid, heptanoic acid is converted to hydroxylated heptanoic acid, octanoic acid is converted to hydroxylated octanoic acid, nonanoic acid is converted to hydroxylated nonanoic acid, decanoic acid is converted to hydroxylated decanoic acid, undecanoic acid is converted to hydroxylated undecanoic acid, dodecanoic acid is converted to hydroxylated dodecanoic acid, tridecanoic acid is converted to hydroxylated tridecanoic acid, tetradecanoic acid is converted to hydroxylated tetradecanoic acid, pentadecanoic acid is converted to hydroxylated pentadecanoic acid, hexadecanoic acid is converted to hydroxylated hexadecanoic acid, heptadecanoic acid is converted to hydroxylated heptadecanoic acid, octadecanoic acid is converted to hydroxylated octadecanoic acid, nonadecanoic acid is converted to hydroxylated nonadecanoic acid, eicosanoic acid is converted to hydroxylated eicosanoic acid, heneicosanoic acid is converted to hydroxylated heneicosanoic acid, docosanoic acid is converted to hydroxylated docosanoic acid, tricosanoic acid is converted to hydroxylated tricosanoic acid, tetracosanoic acid is converted to hydroxylated tetracosanoic acid, pentacosanoic acid is converted to hydroxylated pentacosanoic acid, hexacosanoic acid is converted to hydroxylated hexacosanoic acid, heptacosanoic acid is converted to hydroxylated heptacosanoic acid, octacosanoic acid is converted to hydroxylated octacosanoic acid, nonacosanoic acid is converted to hydroxylated nonacosanoic acid, triacontanoic acid is converted to hydroxylated triacontanoic acid, henatriacontanoic acid is converted to hydroxylated henatriacontanoic acid, dotriacontanoic acid is converted to hydroxylated dotriacontanoic acid, tritriacontanoic acid is converted to hydroxylated tritriacontanoic acid, tetratriacontanoic acid is converted to hydroxylated tetratriacontanoic acid, pentatriacontanoic acid is converted to hydroxylated pentatriacontanoic acid, hexatriacontanoic acid is converted to hydroxylated hexatriacontanoic acid, heptatriacontanoic acid is converted to hydroxylated heptatriacontanoic acid, octatriacontanoic acid is converted to hydroxylated octatriacontanoic acid, nonatriacontanoic acid is converted to hydroxylated nonatriacontanoic acid, and tetracontanoic acid is converted to hydroxylated tetracontanoic acid.

Hydroxy fatty acids, in some embodiments, comprise a hydroxyl group at position ω-1, ω-2, ω-3, or combinations thereof. In some embodiments, the hydroxyl fatty acid comprises a hydroxyl group at position ω-1, ω-2, and ω-3. In some embodiments, the hydroxyl fatty acid comprises a hydroxyl group at position ω-1. In some embodiments, the hydroxyl fatty acid comprises a hydroxyl group at position ω-2. In some embodiments, the hydroxyl fatty acid comprises a hydroxyl group at position ω-3.

In some embodiments, hydroxy fatty acids are contacted with a cell culture. In some embodiments, contacting the hydroxy fatty acids with a cell culture comprises exposing a hydroxy fatty acid with a cell culture for a suitable period sufficient for formation of lactones in the cell culture, if any. In some embodiments, the hydroxy fatty acids are isolated prior to contact with the cell culture. In some embodiments, the hydroxy fatty acids in a medium are contacted with the cell culture.

Cellular Systems

A cellular system refers to any cell or cells that provide for expression of ectopic proteins or heterologous proteins (e.g., CYP450). A cellular system includes, but is not limited to, bacterial cells, yeast cells, plant cells, and animal cells. In some embodiments, the cellular system comprises bacterial cells, yeast cells, or a combination thereof. In some embodiments, the cellular system comprises prokaryotic cells, eukaryotic cells, and combinations thereof. In some embodiments, the cellular system comprises in vitro expression of proteins based on cellular components, such as ribosomes.

Bacterial cells of the present disclosure include, without limitation, *Escherichia* spp., *Streptomyces* spp., *Zymomonas* spp., *Acetobacter* spp., *Citrobacter* spp., *Synechocystis* spp., *Rhizobium* spp., *Clostridium* spp., *Corynebacterium* spp., *Streptococcus* spp., *Xanthomonas* spp., *Lactobacillus* spp., *Lactococcus* spp., *Bacillus* spp., *Alcaligenes* spp., *Pseudomonas* spp., *Aeromonas* spp., *Azotobacter* spp., *Comamonas* spp., *Mycobacterium* spp., *Rhodococcus* spp., *Gluconobacter* spp., *Ralstonia* spp., *Acidithiobacillus* spp., *Microlunatus* spp., *Geobacter* spp., *Geobacillus* spp., *Arthrobacter* spp., *Flavobacterium* spp., *Serratia* spp., *Saccharopolyspora* spp., *Thermus* spp., *Stenotrophomonas* spp., *Chromobacterium* spp., *Sinorhizobium* spp., *Saccharopolyspora* spp., *Agrobacterium* spp., *Pantoea* spp., and *Vibrio natriegens*.

Yeast cells of the present disclosure include, without limitation, engineered *Saccharomyces* spp., *Schizosaccharomyces, Hansenula, Candida, Kluyveromyces, Yarrowia, Candida boidinii*, and *Pichia*. According to the current disclosure, a yeast as claimed herein are eukaryotic, single-celled microorganisms classified as members of the fungus kingdom. Yeasts are unicellular organisms which evolved from multicellular ancestors but with some species useful for the current disclosure being those that have the ability to develop multicellular characteristics by forming strings of connected budding cells known as pseudo hyphae or false hyphae.

In some embodiments, cell pellets are harvested from the cellular system expressing CYP450. In some embodiments, the cell pellets may be resuspended at various concentrations. In some embodiments, the cell pellets are resuspended at a concentration of 1 g/L to 250 g/L. In some embodiments, the cell pellets harvested from the cellular system are resuspended at a concentration of 1 g/L, 10 g/L, 25 g/L, 50 g/L, 75 g/L, 100 g/L, 125 g/L, 150 g/L, 175 g/L, 200 g/L, 225 g/L, or 250 g/L.

Cell Culture

A cell culture refers to any cell or cells that are in a culture. Culturing is the process in which cells are grown under controlled conditions, typically outside of their natural environment. For example, cells, such as yeast cells, may be grown as a cell suspension in liquid nutrient broth. A cell culture includes, but is not limited to, a bacterial cell culture, a yeast cell culture, a plant cell culture, and an animal cell culture. In some embodiments, the cell culture comprises bacterial cells, yeast cells, or a combination thereof.

A bacterial cell culture of the present disclosure comprises bacterial cells including, but not limited to, *Escherichia* spp., *Streptomyces* spp., *Zymomonas* spp., *Acetobacter* spp., *Citrobacter* spp., *Synechocystis* spp., *Rhizobium* spp., *Clostridium* spp., *Corynebacterium* spp., *Streptococcus* spp., *Xanthomonas* spp., *Lactobacillus* spp., *Lactococcus* spp., *Bacillus* spp., *Alcaligenes* spp., *Pseudomonas* spp., *Aeromonas* spp., *Azotobacter* spp., *Comamonas* spp., *Mycobacterium* spp., *Rhodococcus* spp., *Gluconobacter* spp., *Ralstonia* spp., *Acidithiobacillus* spp., *Microlunatus* spp., *Geobacter* spp., *Geobacillus* spp., *Arthrobacter* spp., *Flavobacterium* spp., *Serratia* spp., *Saccharopolyspora* spp., *Thermus* spp., *Stenotrophomonas* spp., *Chromobacterium* spp., *Sinorhizobium* spp., *Saccharopolyspora* spp., *Agrobacterium* spp., *Pantoea* spp., and *Vibrio natriegens*.

A yeast cell culture of the present disclosure comprises yeast cells including, but not limited to *Saccharomyces* spp., *Schizosaccharomyces, Hansenula, Candida, Kluyveromyces, Yarrowia, Candida boidinii*, and *Pichia*.

In some embodiments, a cell culture as described herein is contacted with hydroxy fatty acids as described herein. In some embodiments, a cell culture as described herein is contacted with hydroxy fatty acids as described herein and corn steep liquor, e.g., at a ratio of 1:1 hydroxy fatty acids to corn steep liquor.

In some embodiments, cells are cultured at a temperature of 16° C. to 40° C. For example, cells may be cultured at a temperature of 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C. or 40° C.

In some embodiments, cells are cultured for a period of time of 0.5 hours to 96 hours, or more. For example, cells may be cultured for a period of time of 12, 18, 24, 30, 36, 42, 48, 54, 60, 66, or 72 hours. Typically, cells, such as bacterial cells, are cultured for a period of time of 12 to 24 hours. In some embodiments, cells are cultured for 12 to 24 hours at a temperature of 37° C. In some embodiments, cells are cultured for 12 to 24 hours at a temperature of 16° C.

In some embodiments, cells are cultured to a density of $1\times10^8$ ($OD_{600}<1$) to $2\times10^{11}$ (OD~200) viable cells/ml cell culture medium. In some embodiments, cells are cultured to a density of $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, or $2\times10^{11}$ viable cells/ml. (Conversion factor: OD $1=8\times10^8$ cells/ml).

Lactones

Lactones are cyclic carboxylic esters containing a 1-oxacycloalkane-2-one structure (—(C═O)—O—) or analogues formed from intramolecular esterification. The present invention relates to lactones (for example, γ-lactones and δ-lactones) formed from straight chain hydroxy carboxylic acids in which the hydroxyl group has reacted with the acid group to form a cyclic carboxylic ester.

The International Union of Pure and Applied Chemistry (IUPAC) names of lactones are derived by adding the term "lactone" at the end of the name of the parent acid. The common names of lactones, used more often than IUPAC names, are formed by changing the -ic acid ending by the hydroxy acid to -olactone. Greek letter designates the carbon atom that bears the hydroxy group to close the ring in the parent hydroxyl carboxylic acid. In other words, Greek letter prefix specifies the number of carbon atoms in the heterocycle—that is, the distance between the relevant —OH and the —COOH groups along said backbone of the parent hydroxyl carboxylic acid. The first carbon atom after the carbon in the —COOH group on the parent compound is labelled α, the second will be labeled β, and so forth. Therefore, the Greek letter prefixes also indicate the size of the lactone ring: α-lactone=3-membered ring, β-lactone=4-membered ring, γ-lactone=5-membered ring; and δ-lactone=6-membered ring.

To illustrate, the lactone derived from the cyclization of γ-hydroxybutyric acid is known as 4-hydroxybutanoic acid lactone or γ-butyrolactone. Similarly, 5-hydroxypentanoic acid is referred as δ-hydroxypentanoic acid and the corresponding lactone is known as 5-hydroxypentanoic acid lactone or δ-valerolactone.

Hydroxy Straight Chain Fatty Acids and Subterminal Hydroxy Groups

Straight chain fatty acid consists of a straight hydrocarbon chain that includes, at the end, a carboxyl group (—COOH). It is the presence of this carboxylic acid group that makes this chemical entity an acid. The straight chain fatty acids may optionally have unsaturated bond between the carbon atom. Branched chain fatty acids are usually saturated fatty acids with one or more alkyl branches substituted on the carbon chain.

One or more hydrogen atoms attached to the hydrocarbon back bone of the straight chain fatty acid may also be replaced by a hydroxyl (—OH) group. Straight chain carboxylic acid with one or more hydroxyl groups is referred as a hydroxy carboxylic acid. Ricinoleic acid is a naturally occurring hydroxy carboxylic acid.

The present invention is related to the replacement or substitution of a hydrogen atom in a saturated straight chain fatty acid with a hydroxyl group using a recombinant microbial organism expressing recombinant protein with the hydroxylase enzyme activity. In a preferred embodiment, substitution of the hydroxyl group takes place at one of the —$CH_2$— groups closest to the terminal methyl end group of the straight chain fatty acid. In general terminology, n or ω refers to the methyl end group of the straight chain fatty acid while the number n-x of ω-x refers to the location of the carbon atom on the back bone where x indicates the number of carbons away from the methyl end group. To illustrate, in the example of stearic acid (or octadecanoic acid), a C18:0 straight chain fatty acid with the formula $CH_3(CH_2)_{16}COOH$, ω-3 would mean the fifteenth carbon in the back bone which is three carbon removed from the methyl end group. Similarly, in the same example, ω-1 would mean the seventeenth carbon in the back bone which is one carbon removed from the methyl end group.

As used in the present invention, when a hydroxyl group is introduced into a straight chain fatty acid specifically at positions ω-1, ω-2 and ω-3 using the recombinant DNA technology according to the present invention, the resulting hydroxylated straight chain fatty acid molecule is referred to as a subterminal hydroxy fatty acid, and the hydroxyl group at positions ω-1, ω-2 and ω-3 in such fatty acid molecule are referred as a subterminal hydroxyl groups.

L1

Microbial Culture Media

The microbial organisms useful in the present invention including wild type and recombinant bacterial, yeast and fungal strains are grown in specified culture medium. The microbial culture medium may be minimal growth medium or rich growth medium. The minimal growth medium comprises a fortified mixture of inorganic compounds and one or more organic nutrients such as glucose, sucrose, or glycerol. The rich growth medium comprises yeast extract, peptone and organic nutrient such as dextrose, sucrose or glycerol. In preferred embodiments, the rich growth medium is supplemented with corn steep liquor to enhance the growth of the microbial organisms.

Synthetic Biology

Standard recombinant DNA and molecular cloning techniques used here are well known in the art and are described, for example, by Sambrook, J., Fritsch, E. F. and Maniatis, T. Molecular Cloning: A Laboratory Manual, 2nd ed.; Cold Spring Harbor Laboratory: Cold Spring Harbor, N.Y., 1989 (hereinafter "Maniatis"); and by Silhavy, T. J., Bennan, M. L. and Enquist, L. W. Experiments with Gene Fusions; Cold Spring Harbor Laboratory: Cold Spring Harbor, N.Y., 1984; and Ausubel, F. M. et al., IN Current Protocols in Molecular Biology, published by Greene Publishing and Wiley-Interscience, 1987; (the entirety of each of which is hereby incorporated herein by reference).

Bacterial Production Systems

Expression of proteins in prokaryotes is most often carried out in a bacterial host cell with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, a proteolytic cleavage site is introduced at the junction of the fusion moiety and the recombinant protein to enable separation of the recombinant protein from the fusion moiety subsequent to purification of the fusion protein. Such vectors are within the scope of the present disclosure.

In an embodiment, the expression vector includes those genetic elements for expression of the recombinant polypeptide in bacterial cells. The elements for transcription and translation in the bacterial cell can include a promoter, a coding region for the protein complex, and a transcriptional terminator.

A person of ordinary skill in the art will be aware of the molecular biology techniques available for the preparation of expression vectors. The polynucleotide used for incorporation into the expression vector of the subject technology, as described above, can be prepared by routine techniques such as polymerase chain reaction (PCR).

A number of molecular biology techniques have been developed to operably link DNA to vectors via complementary cohesive termini. In one embodiment, complementary homopolymer tracts can be added to the nucleic acid molecule to be inserted into the vector DNA. The vector and nucleic acid molecule are then joined by hydrogen bonding between the complementary homopolymeric tails to form recombinant DNA molecules.

In an alternative embodiment, synthetic linkers containing one or more restriction sites are used to operably link the polynucleotide of the subject technology to the expression vector. In an embodiment, the polynucleotide is generated by restriction endonuclease digestion. In an embodiment, the nucleic acid molecule is treated with bacteriophage T4 DNA polymerase or *E. coli* DNA polymerase I, enzymes that remove protruding, 3'-single-stranded termini with their 3'-5'-exonucleolytic activities and fill-in recessed 3'-ends with their polymerizing activities, thereby generating blunt-ended DNA segments. The blunt-ended segments are then incubated with a large molar excess of linker molecules in the presence of an enzyme that is able to catalyze the ligation of blunt-ended DNA molecules, such as bacteriophage T4 DNA ligase. Thus, the product of the reaction is a polynucleotide carrying polymeric linker sequences at its ends. These polynucleotides are then cleaved with the appropriate restriction enzyme and ligated to an expression vector that has been cleaved with an enzyme that produces termini compatible with those of the polynucleotide.

Alternatively, a vector having ligation-independent cloning (LIC) sites can be employed. The required PCR amplified polynucleotide can then be cloned into the LIC vector without restriction digest or ligation (Aslanidis and de Jong, Nucl. Acid. Res. 18 6069-74, (1990), Haun, et al, Biotechniques 13, 515-18 (1992), which is incorporated herein by reference to the extent it is consistent herewith).

In an embodiment, in order to isolate and/or modify the polynucleotide of interest for insertion into the chosen plasmid, it is suitable to use PCR. Appropriate primers for use in PCR preparation of the sequence can be designed to isolate the required coding region of the nucleic acid molecule, to add restriction endonuclease or LIC sites and to place the coding region in the desired reading frame.

In an embodiment, a polynucleotide for incorporation into an expression vector of the subject technology is prepared by the use of PCR using appropriate oligonucleotide primers. The coding region is amplified, whilst the primers themselves become incorporated into the amplified sequence product. In an embodiment, the amplification primers contain restriction endonuclease recognition sites, which allow the amplified sequence product to be cloned into an appropriate vector.

The expression vectors can be introduced into plant or microbial host cells by conventional transformation or transfection techniques. Transformation of appropriate cells with an expression vector of the subject technology is accomplished by methods known in the art and typically depends on both the type of vector and cell. Suitable techniques include calcium phosphate or calcium chloride co-precipitation, DEAE-dextran mediated transfection, lipofection, chemoporation or electroporation.

Successfully transformed cells, that is, those cells containing the expression vector, can be identified by techniques well known in the art. For example, cells transfected with an expression vector of the subject technology can be cultured to produce polypeptides described herein. Cells can be examined for the presence of the expression vector DNA by techniques well known in the art.

The host cells can contain a single copy of the expression vector described previously, or alternatively, multiple copies of the expression vector.

In some embodiments, the transformed cell is an animal cell, an insect cell, a plant cell, an algal cell, a fungal cell, or a yeast cell. In some embodiments, the cell is a plant cell selected from the group consisting of: canola plant cell, a rapeseed plant cell, a palm plant cell, a sunflower plant cell, a cotton plant cell, a corn plant cell, a peanut plant cell, a flax plant cell, a sesame plant cell, a soybean plant cell, and a *petunia* plant cell.

Microbial host cell expression systems and expression vectors containing regulatory sequences that direct high-level expression of foreign proteins are well known to those skilled in the art. Any of these could be used to construct vectors for expression of the recombinant polypeptide of the subjection technology in a microbial host cell. These vectors could then be introduced into appropriate microorganisms via transformation to allow for high level expression of the recombinant polypeptide of the subject technology.

Vectors or cassettes useful for the transformation of suitable microbial host cells are well known in the art. Typically the vector or cassette contains sequences directing transcription and translation of the relevant polynucleotide, a selectable marker, and sequences allowing autonomous replication or chromosomal integration. Suitable vectors comprise a region 5' of the polynucleotide which harbors transcriptional initiation controls and a region 3' of the DNA fragment which controls transcriptional termination. It is preferred for both control regions to be derived from genes homologous to the transformed host cell, although it is to be understood that such control regions need not be derived from the genes native to the specific species chosen as a host.

Initiation control regions or promoters, which are useful to drive expression of the recombinant polypeptide in the desired microbial host cell are numerous and familiar to those skilled in the art. Virtually any promoter capable of driving these genes is suitable for the subject technology including but not limited to CYCI, HIS3, GALI, GALIO, ADHI, PGK, PH05, GAPDH, ADCI, TRPI, URA3, LEU2, ENO, TPI (useful for expression in *Saccharomyces*); AOXI (useful for expression in *Pichia*); and lac, trp, JPL, IPR, T7, tac, and trc (useful for expression in *Escherichia coli*).

Termination control regions may also be derived from various genes native to the microbial hosts. A termination site optionally may be included for the microbial hosts described herein.

In plant cells, the expression vectors of the subject technology can include a coding region operably linked to promoters capable of directing expression of the recombinant polypeptide of the subject technology in the desired tissues at the desired stage of development. For reasons of convenience, the polynucleotides to be expressed may comprise promoter sequences and translation leader sequences derived from the same polynucleotide. 3' non-coding sequences encoding transcription termination signals should also be present. The expression vectors may also comprise one or more introns in order to facilitate polynucleotide expression.

For plant host cells, any combination of any promoter and any terminator capable of inducing expression of a coding region may be used in the vector sequences of the subject technology. Some suitable examples of promoters and terminators include those from nopaline synthase (nos), octopine synthase (ocs) and cauliflower mosaic virus (CaMV) genes. One type of efficient plant promoter that may be used is a high-level plant promoter. Such promoters, in operable linkage with an expression vector of the subject technology should be capable of promoting the expression of the vector. High level plant promoters that may be used in the subject technology include the promoter of the small subunit(s) of the ribulose-1,5-bisphosphate carboxylase for example from soybean (Berry-Lowe et al., J. Molecular and App. Gen., 1:483-98 (1982), the entirety of which is hereby incorporated herein to the extent it is consistent herewith), and the promoter of the chlorophyll binding protein. These two promoters are known to be light-induced in plant cells (see, for example, Genetic Engineering of Plants, an Agricultural Perspective, A. Cashmore, Plenum, N.Y. (1983), pages 29-38; Coruzzi, G. et al., THE Journal of Biological Chemistry, 258:1399 (1983), and Dunsmuir, P. et al., Journal of Molecular and Applied Genetics, 2:285 (1983), each of which is hereby incorporated herein by reference to the extent they are consistent herewith).

Analysis of Sequence Similarity Using Identity Scoring

As used herein "sequence identity" refers to the extent to which two optimally aligned polynucleotide or peptide sequences are invariant throughout a window of alignment of components, e.g., nucleotides or amino acids. An "identity fraction" for aligned segments of a test sequence and a reference sequence is the number of identical components which are shared by the two aligned sequences divided by the total number of components in reference sequence segment, i.e., the entire reference sequence or a smaller defined part of the reference sequence.

As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned (with appropriate nucleotide insertions, deletions, or gaps totaling less than 20 percent of the reference sequence over the window of comparison). Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and preferably by computerized implementations of these algorithms such as GAP, BESTFIT, FASTA, and TFASTA available as part of the GCG® Wisconsin Package® (Accelrys Inc., Burlington, MA). An "identity fraction" for aligned segments of a test sequence and a reference sequence is the number of identical components which are shared by the two aligned sequences divided by the total number of components in the reference sequence segment, i.e., the entire reference sequence or a smaller defined part of the reference sequence. Percent sequence identity is represented as the identity fraction multiplied by 100. The comparison of one or more polynucleotide sequences may be to a full-length polynucleotide sequence or a portion thereof, or to a longer polynucleotide sequence. For purposes of this disclosure "percent identity" may also be determined using BLASTX version 2.0 for translated nucleotide sequences and BLASTN version 2.0 for polynucleotide sequences.

The percent of sequence identity is preferably determined using the "Best Fit" or "Gap" program of the Sequence Analysis Software Package™ (Version 10; Genetics Computer Group, Inc., Madison, WI). "Gap" utilizes the algorithm of Needleman and Wunsch (Needleman and Wunsch, Journal of Molecular Biology 48:443-53, 1970) to find the alignment of two sequences that maximizes the number of matches and minimizes the number of gaps. "BestFit" performs an optimal alignment of the best segment of similarity between two sequences and inserts gaps to maximize the number of matches using the local homology algorithm of Smith and Waterman (Smith and Waterman, Advances in Applied Mathematics, 2:482-489, 1981, Smith et al., Nucleic Acids Research 11:2205-2220, 1983). The percent identity is most preferably determined using the "Best Fit" program.

Useful methods for determining sequence identity are also disclosed in the Basic Local Alignment Search Tool (BLAST) programs which are publicly available from National Center Biotechnology Information (NCBI) at the National Library of Medicine, National Institute of Health, Bethesda, Md. 20894; see BLAST Manual, Altschul et al., NCBI, NLM, NIH; Altschul et al., J. Mol. Biol. 215:403-10 (1990); version 2.0 or higher of BLAST programs allows the introduction of gaps (deletions and insertions) into alignments; for peptide sequence BLASTX can be used to determine sequence identity; and, for polynucleotide sequence BLASTN can be used to determine sequence identity.

As used herein, the term "substantial percent sequence identity" refers to a percent sequence identity of at least about 70% sequence identity, at least about 80% sequence identity, at least about 85% identity, at least about 90% sequence identity, or even greater sequence identity, such as about 98% or about 99% sequence identity. Thus, one embodiment of the disclosure is a polynucleotide molecule that has at least about 70% sequence identity, at least about 80% sequence identity, at least about 85% identity, at least about 90% sequence identity, or even greater sequence identity, such as about 98% or about 99% sequence identity with a polynucleotide sequence described herein. Polynucleotide molecules that have the activity of the Cytochrome P450 genes of the current disclosure are capable of directing the production of a variety of γ- and delta-lactones. Such polynucleotide molecules can have a substantial percent sequence identity to the polynucleotide sequences provided herein and are encompassed within the scope of this disclosure.

Identity and Similarity

Identity is the fraction of amino acids that are the same between a pair of sequences after an alignment of the sequences (which can be done using only sequence information or structural information or some other information, but usually it is based on sequence information alone), and similarity is the score assigned based on an alignment using some similarity matrix. The similarity index can be any one of the following BLOSUM62, PAM250, or GONNET, or any matrix used by one skilled in the art for the sequence alignment of proteins.

Identity is the degree of correspondence between two sub-sequences (no gaps between the sequences). An identity of 25% or higher implies similarity of function, while 18-25% implies similarity of structure or function. Keep in mind that two completely unrelated or random sequences (that are greater than 100 residues) can have higher than 20% identity. Similarity is the degree of resemblance between two sequences when they are compared. This is dependent on their identity.

Explanation of Terms Used Herein

"Coding sequence" is to be given its ordinary and customary meaning to a person of ordinary skill in the art, and is used without limitation to refer to a DNA sequence that encodes for a specific amino acid sequence.

"Protein Expression". Protein production can occur after gene expression. It consists of the stages after DNA has been transcribed to messenger RNA (mRNA). The mRNA is then translated into polypeptide chains, which are ultimately folded into proteins. DNA is present in the cells through transfection—a process of deliberately introducing nucleic acids into cells. The term is often used for non-viral methods in eukaryotic cells. It may also refer to other methods and cell types, although other terms are preferred: "transformation" is more often used to describe non-viral DNA transfer in bacteria, non-animal eukaryotic cells, including plant cells. In animal cells, transfection is the preferred term as transformation is also used to refer to progression to a cancerous state (carcinogenesis) in these cells. Transduction is often used to describe virus-mediated DNA transfer. Transformation, transduction, and viral infection are included under the definition of transfection for this application.

As used herein, the singular forms "a, an" and "the" include plural references unless the content clearly dictates otherwise.

To the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

The term "complementary" is to be given its ordinary and customary meaning to a person of ordinary skill in the art and is used without limitation to describe the relationship between nucleotide bases that are capable to hybridizing to one another. For example, with respect to DNA, adenosine is complementary to thymine and cytosine is complementary to guanine. Accordingly, the subjection technology also includes isolated nucleic acid fragments that are complementary to the complete sequences as reported in the accompanying Sequence Listing as well as those substantially similar nucleic acid sequences.

The terms "nucleic acid" and "nucleotide" are to be given their respective ordinary and customary meanings to a person of ordinary skill in the art and are used without limitation to refer to deoxyribonucleotides or ribonucleotides and polymers thereof in either single- or double-stranded form. Unless specifically limited, the term encompasses nucleic acids containing known analogues of natural nucleotides that have similar binding properties as the reference nucleic acid and are metabolized in a manner similar to naturally-occurring nucleotides. Unless otherwise indicated, a particular nucleic acid sequence also implicitly encompasses conservatively modified or degenerate variants thereof (e.g., degenerate codon substitutions) and complementary sequences, as well as the sequence explicitly indicated.

The term "isolated" is to be given its ordinary and customary meaning to a person of ordinary skill in the art, and when used in the context of an isolated nucleic acid or an isolated polypeptide, is used without limitation to refer to a nucleic acid or polypeptide that, by the hand of man, exists apart from its native environment and is therefore not a product of nature. An isolated nucleic acid or polypeptide can exist in a purified form or can exist in a non-native environment such as, for example, in a transgenic host cell.

The term "degenerate variant" refers to a nucleic acid sequence having a residue sequence that differs from a reference nucleic acid sequence by one or more degenerate codon substitutions. Degenerate codon substitutions can be achieved by generating sequences in which the third position of one or more selected (or all) codons is substituted with mixed base and/or deoxyinosine residues. A nucleic acid sequence and all of its degenerate variants will express the same amino acid or polypeptide.

The terms "polypeptide," "protein," and "peptide" are to be given their respective ordinary and customary meanings to a person of ordinary skill in the art; the three terms are sometimes used interchangeably, and are used without limitation to refer to a polymer of amino acids, or amino acid analogs, regardless of its size or function. Although "protein" is often used in reference to relatively large polypeptides, and "peptide" is often used in reference to small polypeptides, usage of these terms in the art overlaps and varies. The term "polypeptide" as used herein refers to peptides, polypeptides, and proteins, unless otherwise noted. The terms "protein," "polypeptide," and "peptide" are used interchangeably herein when referring to a polynucleotide product. Thus, exemplary polypeptides include polynucleotide products, naturally occurring proteins, homologs, orthologs, paralogs, fragments and other equivalents, variants, and analogs of the foregoing.

The terms "polypeptide fragment" and "fragment," when used in reference to a reference polypeptide, are to be given their ordinary and customary meanings to a person of ordinary skill in the art and are used without limitation to refer to a polypeptide in which amino acid residues are deleted as compared to the reference polypeptide itself, but where the remaining amino acid sequence is usually identical to the corresponding positions in the reference polypeptide. Such deletions can occur at the amino-terminus or carboxy-terminus of the reference polypeptide, or alternatively both.

The term "functional fragment" of a polypeptide or protein refers to a peptide fragment that is a portion of the full-length polypeptide or protein, and has substantially the same biological activity, or carries out substantially the same function as the full-length polypeptide or protein (e.g., carrying out the same enzymatic reaction).

The terms "variant polypeptide," "modified amino acid sequence" or "modified polypeptide," which are used interchangeably, refer to an amino acid sequence that is different from the reference polypeptide by one or more amino acids, e.g., by one or more amino acid substitutions, deletions, and/or additions. In an aspect, a variant is a "functional variant" which retains some or all of the ability of the reference polypeptide.

The term "functional variant" further includes conservatively substituted variants. The term "conservatively substituted variant" refers to a peptide having an amino acid sequence that differs from a reference peptide by one or more conservative amino acid substitutions and maintains some or all of the activity of the reference peptide. A "conservative amino acid substitution" is a substitution of an amino acid residue with a functionally similar residue. Examples of conservative substitutions include the substitution of one non-polar (hydrophobic) residue such as isoleucine, valine, leucine or methionine for another; the substitution of one charged or polar (hydrophilic) residue for another such as between arginine and lysine, between glutamine and asparagine, between threonine and serine; the substitution of one basic residue such as lysine or arginine for another; or the substitution of one acidic residue, such as aspartic acid or glutamic acid for another; or the substitution of one aromatic residue, such as phenylalanine, tyrosine, or tryptophan for another. Such substitutions are expected to have little or no effect on the apparent molecular weight or isoelectric point of the protein or polypeptide. The phrase "conservatively substituted variant" also includes peptides wherein a residue is replaced with a chemically-derivatized residue, provided that the resulting peptide maintains some or all of the activity of the reference peptide as described herein.

The term "variant," in connection with the polypeptides of the subject technology, further includes a functionally active polypeptide having an amino acid sequence at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, and even 100% identical to the amino acid sequence of a reference polypeptide.

The term "homologous" in all its grammatical forms and spelling variations refers to the relationship between polynucleotides or polypeptides that possess a "common evolutionary origin," including polynucleotides or polypeptides from super families and homologous polynucleotides or proteins from different species (Reeck et al., CELL 50:667, 1987). Such polynucleotides or polypeptides have sequence homology, as reflected by their sequence similarity, whether in terms of percent identity or the presence of specific amino acids or motifs at conserved positions. For example, two homologous polypeptides can have amino acid sequences that are at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 900 at least 91%, at least 92%, at least 93%, at least 94%, at least 95%, at least 96%, at least 97%, at least 98%, at least 99%, and even 100% identical.

"Suitable regulatory sequences" is to be given its ordinary and customary meaning to a person of ordinary skill in the art, and is used without limitation to refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" is to be given its ordinary and customary meaning to a person of ordinary skill in the art, and is used without limitation to refer to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters, which cause a gene to be expressed in most cell types at most times, are commonly referred to as "constitutive promoters." It is further recognized that since in most cases the exact boundaries of regulatory sequences have not been completely defined, DNA fragments of different lengths may have identical promoter activity.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression" as used herein, is to be given its ordinary and customary meaning to a person of ordinary skill in the art, and is used without limitation to refer to the transcription and stable accumulation of sense (mRNA) or antisense RNA derived from the nucleic acid fragment of the subject technology. "Over-expression" refers to the production of a gene product in transgenic or recombinant organisms that exceeds levels of production in normal or non-transformed organisms.

"Transformation" is to be given its ordinary and customary meaning to a person of reasonable skill in the field, and is used without limitation to refer to the transfer of a polynucleotide into a target cell for further expression by that cell. The transferred polynucleotide can be incorporated into the genome or chromosomal DNA of a target cell, resulting in genetically stable inheritance, or it can replicate independent of the host chromosomal. Host organisms containing the transformed nucleic acid fragments are referred to as "transgenic" or "recombinant" or "transformed" organisms.

The terms "transformed," "transgenic," and "recombinant," when used herein in connection with host cells, are to be given their respective ordinary and customary meanings to a person of ordinary skill in the art, and are used without limitation to refer to a cell of a host organism, such as a plant or microbial cell, into which a heterologous nucleic acid molecule has been introduced. The nucleic acid molecule can be stably integrated into the genome of the host cell, or the nucleic acid molecule can be present as an extrachromosomal molecule. Such an extrachromosomal molecule can be auto-replicating. Transformed cells, tissues, or subjects are understood to encompass not only the end product of a transformation process, but also transgenic progeny thereof.

The terms "recombinant," "heterologous," and "exogenous," when used herein in connection with polynucleotides, are to be given their ordinary and customary meanings to a person of ordinary skill in the art, and are used without limitation to refer to a polynucleotide (e.g., a DNA sequence or a gene) that originates from a source foreign to the particular host cell or, if from the same source, is modified from its original form. Thus, a heterologous gene in a host cell includes a gene that is endogenous to the particular host cell but has been modified through, for example, the use of site-directed mutagenesis or other recombinant techniques. The terms also include non-naturally occurring multiple copies of a naturally occurring DNA sequence. Thus, the terms refer to a DNA segment that is foreign or heterologous to the cell, or homologous to the cell but in a position or form within the host cell in which the element is not ordinarily found.

Similarly, the terms "recombinant," "heterologous," and "exogenous," when used herein in connection with a polypeptide or amino acid sequence, means a polypeptide or amino acid sequence that originates from a source foreign to the particular host cell or, if from the same source, is modified from its original form. Thus, recombinant DNA segments can be expressed in a host cell to produce a recombinant polypeptide.

The terms "plasmid," "vector," and "cassette" are to be given their respective ordinary and customary meanings to a person of ordinary skill in the art and are used without limitation to refer to an extra chromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitate transformation of a particular host cell. "Expression cassette" refers to a specific vector containing a foreign gene and having elements in addition to the foreign gene that allow for enhanced expression of that gene in a foreign host.

The term "cellular system" as used herein refers to any cells that provide for the expression of ectopic proteins. In some embodiments, the cellular system comprises bacterial cells, yeast cells, plant cells, and animal cells. In some embodiments, the cellular system, comprises prokaryotic cells and/or eukaryotic cells. In some embodiments, the cellular system comprises in vitro expression of proteins based on cellular components, such as ribosomes.

The term "cell culture" as used herein refers to a composition comprising cells. In some embodiments, the cell culture is a liquid (e.g., a broth culture). In some embodiments, the cell culture is a solid (e.g., a stab culture). In some embodiments, the cell culture comprises bacterial cells, yeast cells, plant cells, and animal cells. In some embodiments, the cell culture comprises prokaryotic cells and/or eukaryotic cells. In some embodiments, the cell culture comprises in vitro expression of proteins based on cellular components, such as ribosomes.

The terms "incubating" and "incubation" as used herein refers to a process of mixing two or more chemical or biological entities (such as a chemical compound and an enzyme) and allowing them to interact under conditions favorable for producing a new chemical entity such as hydroxy fatty acid (e.g., a subterminal hydroxy fatty acid) as described herein or a lactone (e.g., a gamma-lactone, a delta-lactone, or combinations thereof) as described herein.

"Percent (%) amino acid sequence identity" with respect to the variant polypeptide sequences of the subject technology refers to the percentage of amino acid residues in a candidate sequence that are identical with the amino acid residues of a reference polypeptide, after aligning the sequences and introducing gaps, if necessary, to achieve the maximum percent sequence identity, and not considering any conservative substitutions as part of the sequence identity.

Alignment for purposes of determining percent amino acid sequence identity can be achieved in various ways that are within the skill in the art, for instance, using publicly available computer software such as BLAST, BLAST-2, ALIGN, ALIGN-2 or Megalign (DNASTAR) software. Those skilled in the art can determine appropriate parameters for measuring alignment, including any algorithms needed to achieve maximal alignment over the full-length of the sequences being compared. For example, the % amino acid sequence identity may be determined using the sequence comparison program NCBI-BLAST2. The NCBI-BLAST2 sequence comparison program may be downloaded from ncbi.nlm.nih.gov. NCBI BLAST2 uses several search parameters, wherein all of those search parameters are set to default values including, for example, unmask yes, strand=all, expected occurrences 10, minimum low complexity length=15/5, multi-pass e-value=0.01, constant for multi-pass=25, dropoff for final gapped alignment=25 and scoring matrix=BLOSUM62. In situations where NCBI-BLAST2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y where X is the number of amino acid residues scored as identical matches by the sequence alignment program NCBI-BLAST2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

In this sense, techniques for determining amino acid sequence "similarity" are well known in the art. In general, "similarity" refers to the exact amino acid to amino acid comparison of two or more polypeptides at the appropriate place, where amino acids are identical or possess similar chemical and/or physical properties such as charge or hydrophobicity. A so-termed "percent similarity" may then be determined between the compared polypeptide sequences. Techniques for determining nucleic acid and amino acid sequence identity also are well known in the art and include determining the nucleotide sequence of the mRNA for that gene (usually via a cDNA intermediate) and determining the amino acid sequence encoded therein, and comparing this to a second amino acid sequence. In general, "identity" refers to an exact nucleotide to nucleotide or amino acid to amino acid correspondence of two polynucleotides or polypeptide sequences, respectively. Two or more polynucleotide sequences can be compared by determining their "percent identity", as can two or more amino acid sequences. The programs available in the Wisconsin Sequence Analysis Package, Version 8 (available from Genetics Computer Group, Madison, Wis.), for example, the GAP program, are capable of calculating both the identity between two polynucleotides and the identity and similarity between two polypeptide sequences, respectively. Other programs for calculating identity or similarity between sequences are known by those skilled in the art.

An amino acid position "corresponding to" a reference position refers to a position that aligns with a reference sequence, as identified by aligning the amino acid sequences. Such alignments can be done by hand or by using well-known sequence alignment programs such as ClustalW2, Blast 2, etc.

Unless specified otherwise, the percent identity of two polypeptide or polynucleotide sequences refers to the percentage of identical amino acid residues or nucleotides across the entire length of the shorter of the two sequences.

"Transformation" is used according to its ordinary and customary meaning as understood by a person of ordinary skill in the art, and is used without limitation to refer to the transfer of a polynucleotide into a target cell. The transferred polynucleotide can be incorporated into the genome or chromosomal DNA of a target cell, resulting in genetically stable inheritance, or it can replicate independent of the host chromosomal. Host organisms containing the transformed nucleic acid fragments are referred to as "transgenic" or "recombinant" or "transformed" organisms.

The terms "recombinant," "heterologous," and "exogenous," when used herein in connection with polynucleotides, are used according to their ordinary and customary meanings as understood by a person of ordinary skill in the art, and are used without limitation to refer to a polynucleotide (e.g., a DNA sequence or a gene) that originates from a source foreign to the particular host cell or, if from the same source, is modified from its original form. Thus, a heterologous gene in a host cell includes a gene that is endogenous to the particular host cell but has been modified through, for example, the use of site-directed mutagenesis or other recombinant techniques. The terms also include non-naturally occurring multiple copies of a naturally occurring DNA sequence. Thus, the terms refer to a DNA segment that is foreign or heterologous to the cell, or homologous to the cell but in a position or form within the host cell in which the element is not ordinarily found.

Similarly, the terms "recombinant," "heterologous," and "exogenous," when used herein in connection with a polypeptide or amino acid sequence, means a polypeptide or amino acid sequence that originates from a source foreign to the particular host cell or, if from the same source, is modified from its original form. Thus, recombinant DNA segments can be expressed in a host cell to produce a recombinant polypeptide.

Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, the preferred materials and methods are described below.

The disclosure will be more fully understood upon consideration of the following non-limiting Examples. It should be understood that these Examples, while indicating preferred embodiments of the subject technology, are given by way of illustration only. From the above discussion and these Examples, one skilled in the art can ascertain the essential characteristics of the subject technology, and without departing from the spirit and scope thereof, can make various changes and modifications of the subject technology to adapt it to various uses and conditions.

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features. From the above description, one skilled in the art can easily ascertain the essential characteristics of the present disclosure, and without departing from the spirit and scope thereof, can make various changes and modifications of the present disclosure to adapt it to various usages and conditions. Thus, other embodiments are also within the claims.

EQUIVALENTS AND SCOPE

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present disclosure, as defined in the following claims.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. It should be appreciated that embodiments described in this document using an open-ended transitional phrase (e.g., "comprising") are also contemplated, in alternative embodiments, as "consisting of" and "consisting essentially of" the feature described by the open-ended transitional phrase. For example, if the disclosure describes "a composition comprising A and B", the disclosure also contemplates the alternative embodiments "a composition consisting of A and B" and "a composition consisting essentially of A and B".

Furthermore, the present disclosure encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the present disclosure, or aspects of the present disclosure, is/are referred to as comprising particular elements and/or features, certain embodiments of the present disclosure or aspects of the present disclosure consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the present disclosure, to the tenth of the unit of the lower limit of the range, unless the context clearly dictates otherwise.

This application refers to various journal articles, and other publications, all of which are incorporated herein by reference. All references, patents and patent applications disclosed herein are incorporated by reference with respect to the subject matter for which each is cited, which in some cases may encompass the entirety of the document. If there is a conflict between any of the incorporated references and the instant specification, the specification shall control. In addition, any particular embodiment of the present disclosure that falls within the prior art may be explicitly excluded from any one or more of the claims. Because such embodiments are deemed to be known to one of ordinary skill in the art, they may be excluded even if the exclusion is not set forth explicitly herein. Any particular embodiment of the present disclosure can be excluded from any claim, for any reason, whether or not related to the existence of prior art.

EXAMPLES

Example 1

Cloning of M. thermophile CYP505A30 and *E. coli* Icd

The amino acid sequence of a BM3 homolog of *Myceliophthora* thermophile (CYP505A30) was obtained from UniProt (www.uniprot.org/uniprot/G2QDZ3.fasta) and the corresponding gene was codon optimized for expression in *Escherichia coli* and synthesized by GenScript (Piscataway, NJ). The nucleotide sequence of CYP505A30 from M. thermophile with codon-optimization for *E. coli* expression is provided as SEQ ID NO: 1. The amino acid sequence of CYP505A30 is provided as SEQ ID NO: 3.

The resulting gene product was cloned into pETDuet-1 vector ($AMP^+$, Novagen) through NdeI and XhoI sites. The construct was transformed into BL21 (DE3) cells for expression. To enhance CYP505A30 activity in *E. coli*, an isocitrate dehydrogenase (Icd)-mediated NADPH regenerating system was coupled with CYP505A30. Primers ICD-F, 5'-ggaattcCATatgGAAAGTAAAGTAGTTGT (SEQ ID NO: 7) and ICD-R, 5'-ccgCTCGAGttaCATGTTTTCGATGATCGCGT (SEQ ID NO: 8) were used to amplify the icd gene by PCR from the genome of *E. coli* K-12 substr. MG1655. The nucleotide sequence of icd from *E. coli* K-12 substr. MG1655 is provided as SEQ ID NO: 2. The corresponding amino acid sequence is provided as SEQ ID NO: 4.

The resulting PCR product was subcloned into pCDFDuet-1 vector ($Spect^+$, Novagen) through NdeI and XhoI sites. The construct was used to transformed BL21 (DE3) cells overexpressing CYP505A30 and the transformants were selected on LB ($AMP^+Spect^+$) plates.

The resulting vectors are used to overexpress M. thermophile CYP505A30 and *E. coli* Icd in *E. coli* cells.

Example 2

Production of Gamma- and Delta-Lactones Using *E. coli* Cells Overexpressing M. Thermophile CYP505A30 and *E. coli* Icd This example demonstrates the use of *E. coli* cells overexpressing M. thermophile CYP505A30 and *E. coli* Icd in the bioconversion of short chain fatty acids into gamma- and delta-lactones via a subterminal hydroxy fatty acid intermediate.

To produce subterminal (i.e., omega-1 (ω-1), omega-2 (ω-2), and omega-3 (ω-3)) hydroxy fatty acids from corresponding short chain fatty acids, *E. coli* cells overexpressing CYP505A30 and Icd were incubated with medium comprising the short chain fatty acids as substrates.

In a typical experiment, an overnight culture was used to inoculate liquid LB medium (2%) containing 100 mg/L of carbenicillin and 100 mg/L of spectinomycin. The culture was first grown at 37° C. to an $OD_{600}$ of 0.6 and cooled down to 16° C. Then 1 mM IPTG was added to induce protein expression. After 16 h of incubation at 16° C., cells were harvested by centrifugation.

Harvested cell pellets were re-suspended at a concentration of 100 g/L fresh weight in 100 mM potassium phosphate buffer (pH7.0) containing 0.1% Tween 40. Then 3 g/L of lauric acid (C12:0) or 3 g/L of tridecanoic acid (C13:0) together with 10 g/L of isocitric acid trisodium salt were added for biotransformation at 30° C. in a shaker. Samples were taken at different reaction times and analyzed by GC/FID.

GC/FID analysis was conducted on Shimadzu GC-2014 system. The analytical column is Restek RXi-5 ms (thickness 0.25 μm; length 30 m; diameter 0.25 mm) and the injection temperature is 240° C. under split mode. The temperature gradient is 0-3 min, 100° C.; 3-9 min 100° C.-280° C., a gradient of 30; 9-12 min, 280° C.

Figure 2A:
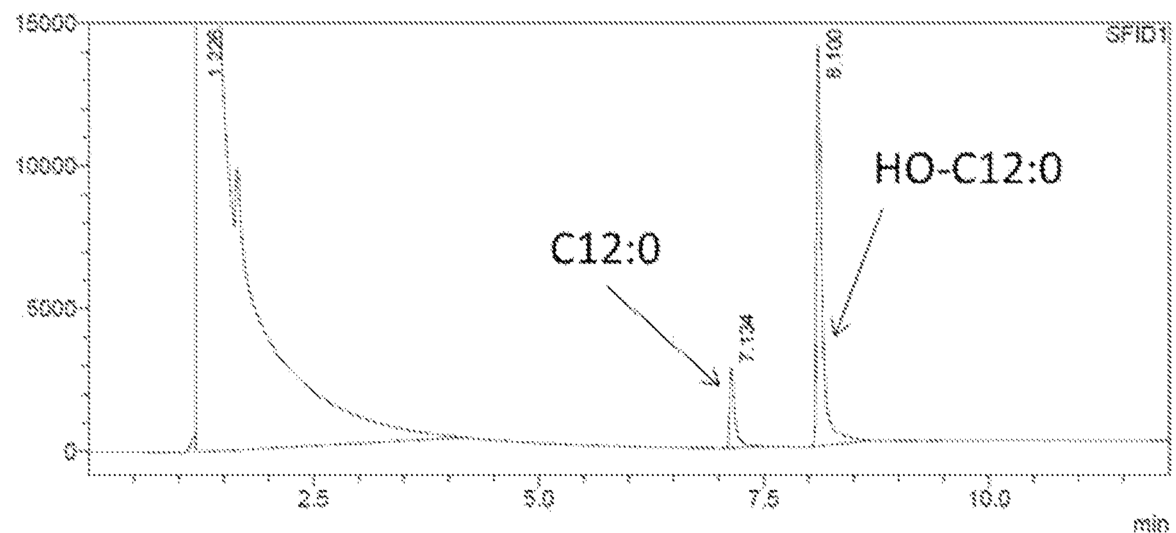
FIG. 2A shows GC/MS spectra confirming production of subterminal hydroxy fatty acid HO-C12:0 from the corresponding straight chain fatty acid C12:0 in a cellular system in which M. thermophile CYP505A30 and *E. coli* icd were overexpressed. Samples were taken 4 hours after bioconversion.
Figure 2B:
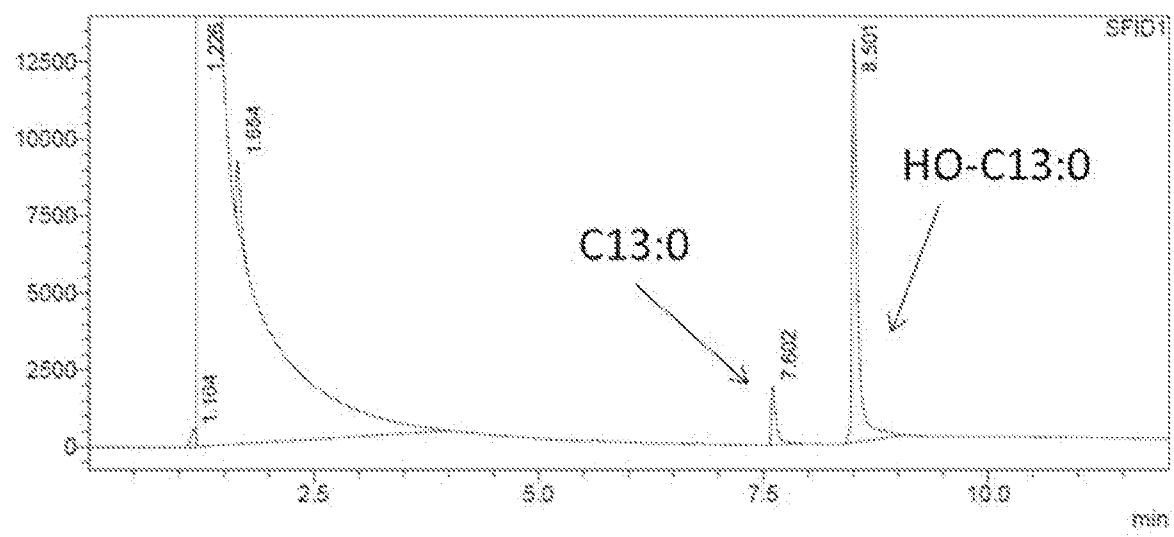
FIG. 2B shows GC/MS spectra confirming production of subterminal hydroxy fatty acid HO-C13:0 from the corresponding straight chain fatty acid C13:0 in a cellular system in which M. thermophile CYP505A30 and *E. coli* icd were overexpressed. Samples were taken 4 hours after bioconversion.

As shown in FIG. 2A and FIG. 2B, HO-C12:0 and HO-C13:0 were efficiently produced from the corresponding carboxylic acids C12:0 (dodecanoic acid, also known as lauric acid) and C13:0 (tridecanoic acid, also known as tridecylic acid) by *E. coli* cells modified according to the procedures described in Example 1. According to Baker et al. (2017), CYP505A30 catalyzed hydroxylation of straight chain fatty acids at the ω-1 to ω-3 positions. However, FIGS.

2A-2B show single peaks because GC/FID cannot separate ω-1 to ω-3 hydroxy fatty acids in the absence of derivatization. As a result, the peaks represent a mixture of ω-1 to ω-3 hydroxy fatty acids.

These results evidence production of ω-1 to ω-3 hydroxy fatty acids from corresponding fatty acids by re-suspended *E. coli* cells overexpressing M. thermophile CYP505A30 and *E. coli* Icd.

To produce gamma-lactones (5-membered ring) and delta-lactones (6-membered ring) from subterminal hydroxy fatty acids, the mixture of ω-1 to ω-3 hydroxy fatty acids from the previous step was first isolated from the re-suspended *E. coli* cells then inoculated with a *Candida boidinii* culture.

As an example of producing lactones from hydroxy fatty acids, the mixture of HO-C12:0 and the mixture of HO-C13:0, respectively, was mixed with 60 g/L of corn steep liquor (CSL) at a 1:1 ratio, and the resulting medium was autoclaved at 121° C. for 20 min. The media was named as CYP505A30C12 or CYP505A30C13 for C12:0 and C13:0 bioconversion, respectively. Then the medium was inoculated with an overnight yeast culture (e.g., *Candida boidinii*), and the yeast culture was grown in a 30° C. shaker. Samples were taken daily after inoculation and analyzed as described herein.

To analyze γ-lactone production, 0.5 ml *E. coli* culture was taken and 10 μl 2N HCl was added. The acidified culture was extracted with 0.5 ml ethyl acetate with shaking at room temperature for 60 min. After centrifugation at 14,000 rpm for 15 min, the ethyl acetate phase was used for GC/MS or GC/FID analysis.

GC/MS analysis was conducted on Shimadzu GC-2010 system coupled with GCMS-QP2010S detector. The analytical column is SHRXI-5 MS (thickness 0.25 μm; length 30 m; diameter 0.25 mm) and the injection temperature is 265° C. under split mode. The temperature gradient is 0-3 min 80° C.; 3-8.7 min 120° C. to 263° C., a gradient of 25; 8.7-10.7 min, 263° C.

Figure 3:
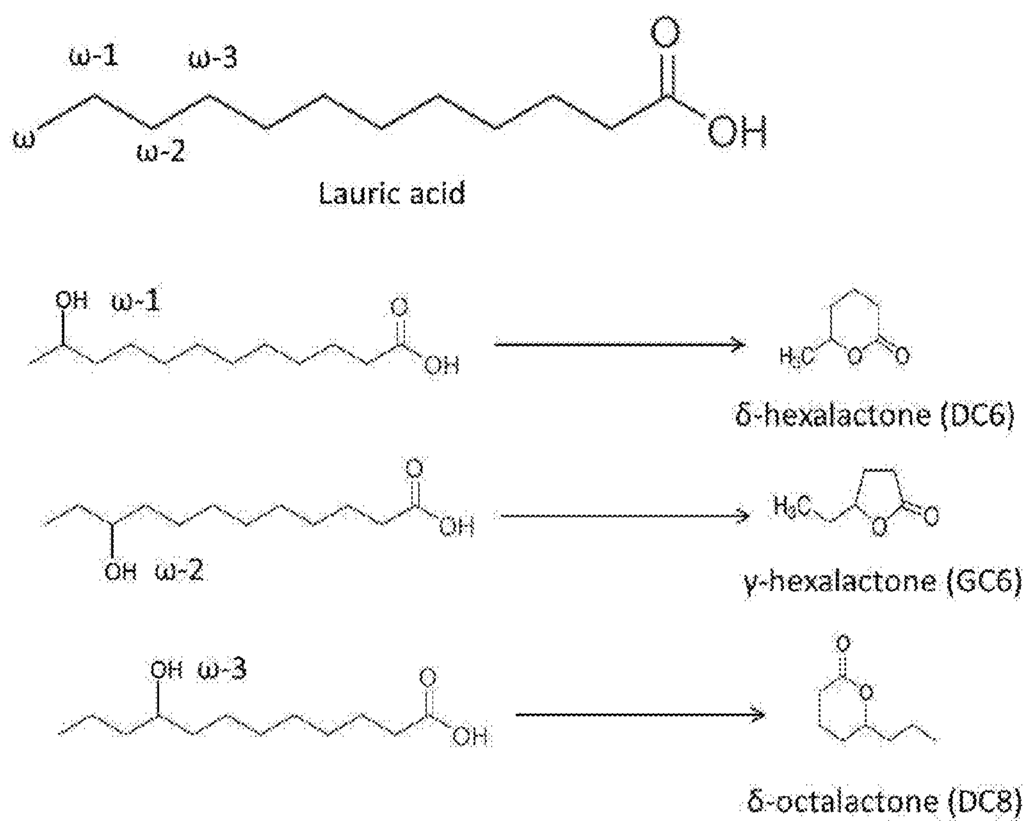
FIG. 3 illustrates the production of δ-hexalactone (DC6), γ-hexalactone (GC6), and 8-octalactone (DC8) from lauric acid (C12:0).
Figure 4A:
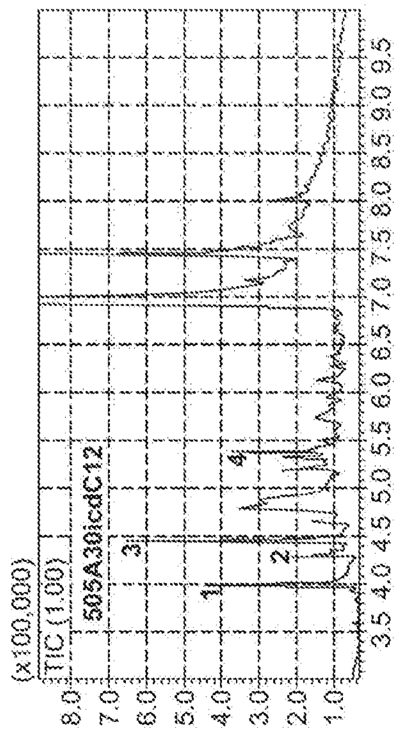
FIGS. 4A, 4B, 4C, 4D, and 4E show GC/MS spectra confirming production of gamma- and delta-lactones from subterminal hydroxy fatty acids HO-12:0.
Figure 4B:
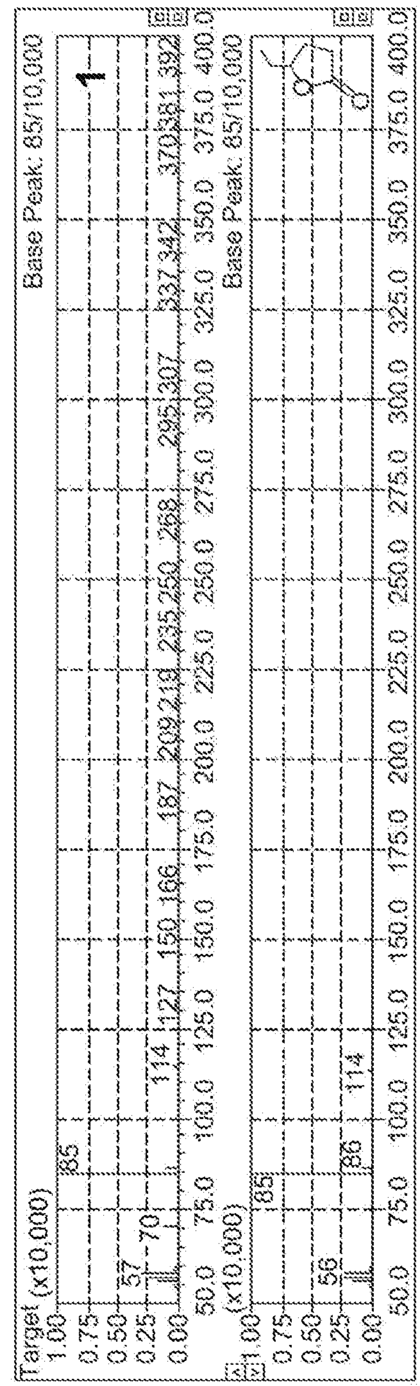
Figure 4C:
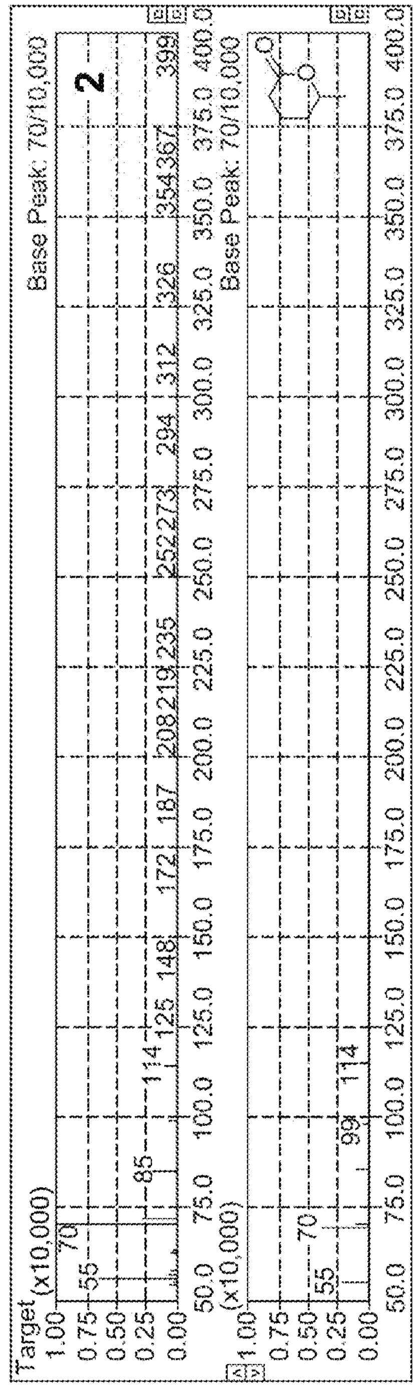
Figure 4D:
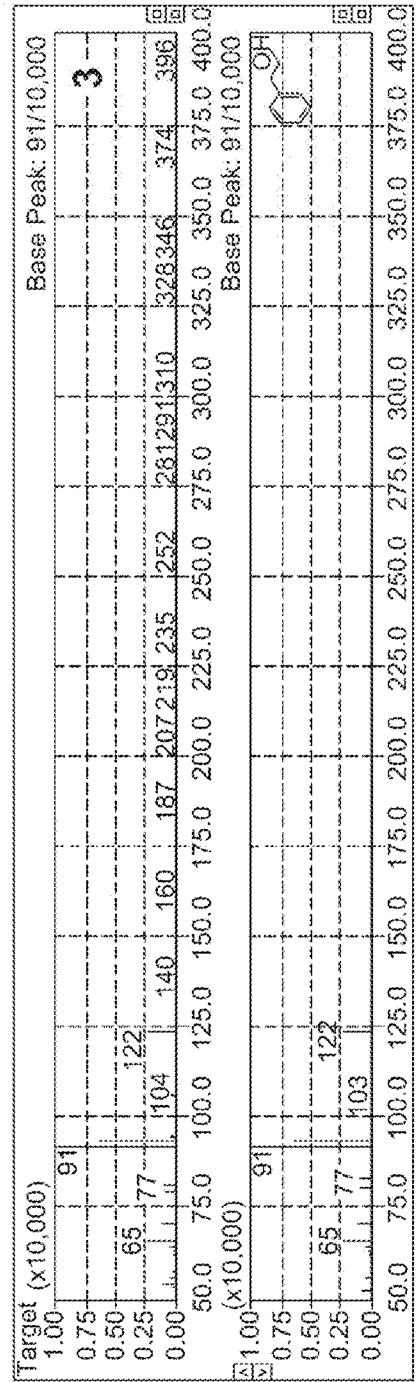
Figure 4E:
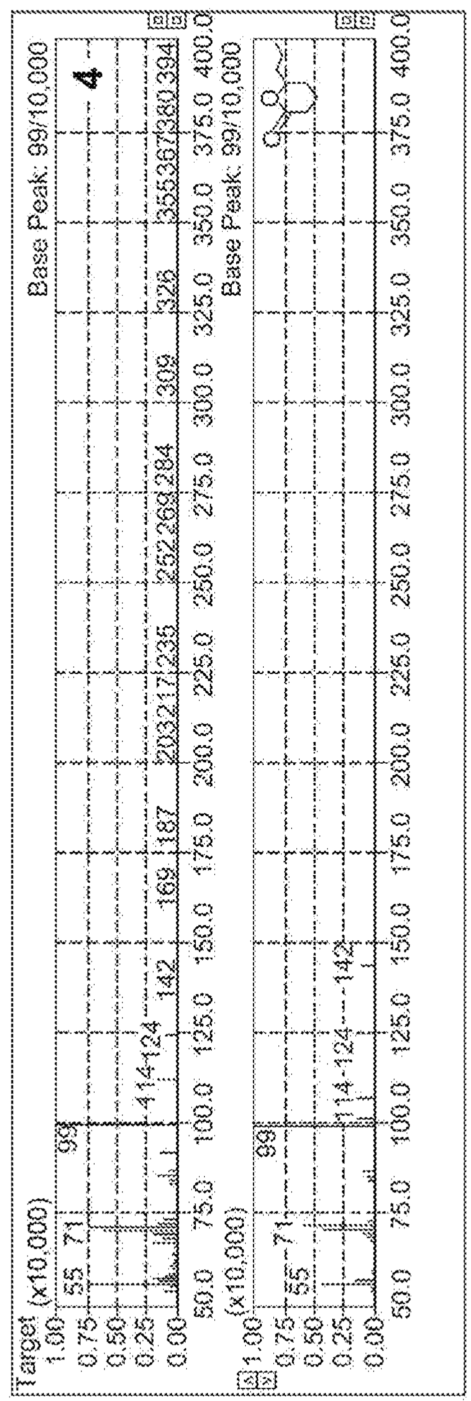

As shown in FIG. 3, if the initial starting fatty acid has an even number of carbons such as C12:0 (dodecanoic acid, also known as lauric acid), after β-oxidation in yeast, the predicted products would be δ-hexalactone (DC6) from the ω-1 hydroxy fatty acid intermediate, γ-hexalactone (GC6) from the ω-2 hydroxy fatty acid intermediate, and δ-octalactone (DC8) from the ω-3 hydroxy fatty acid intermediate. This is because in each round of β-oxidation, 2 carbon atoms are removed from the hydroxy fatty acid intermediate. Depending on the position of the OH group in the hydroxy fatty acid, there can be 9, 8, or 7 intervening carbon atoms between the hydroxylated carbon atom and the carboxylated carbon atom in the hydroxy fatty acid. Once β-oxidation has removed enough pairs of carbon atoms such that there are either 2 or 3 intervening carbon atoms remaining, favorable kinetics lead to cyclization into the lactone product (a γ-lactone if there are 2 intervening carbon atoms remaining, and a δ-lactone if there are 3 intervening carbon atoms remaining.

FIG. 4 shows the spectra from GC/MS analysis obtained with CYP505A30C12 (containing ω-1 to ω-3 hydroxy lauric acid) following incubation with *Candida boidinii*. Referring to FIG. 4A, peaks 1, 2, 3, and 4 were analyzed. After comparing the retention times to those of known standards, peak 1 was identified to be the γ-hexalactone GC6, peak 2 was identified to be the δ-hexalactone DC6, and peak 4 was identified to be the δ-octalactone DC8. Peak 3 was identified to be phenethyl alcohol, which is a metabolite of yeast metabolism.

Figure 5:
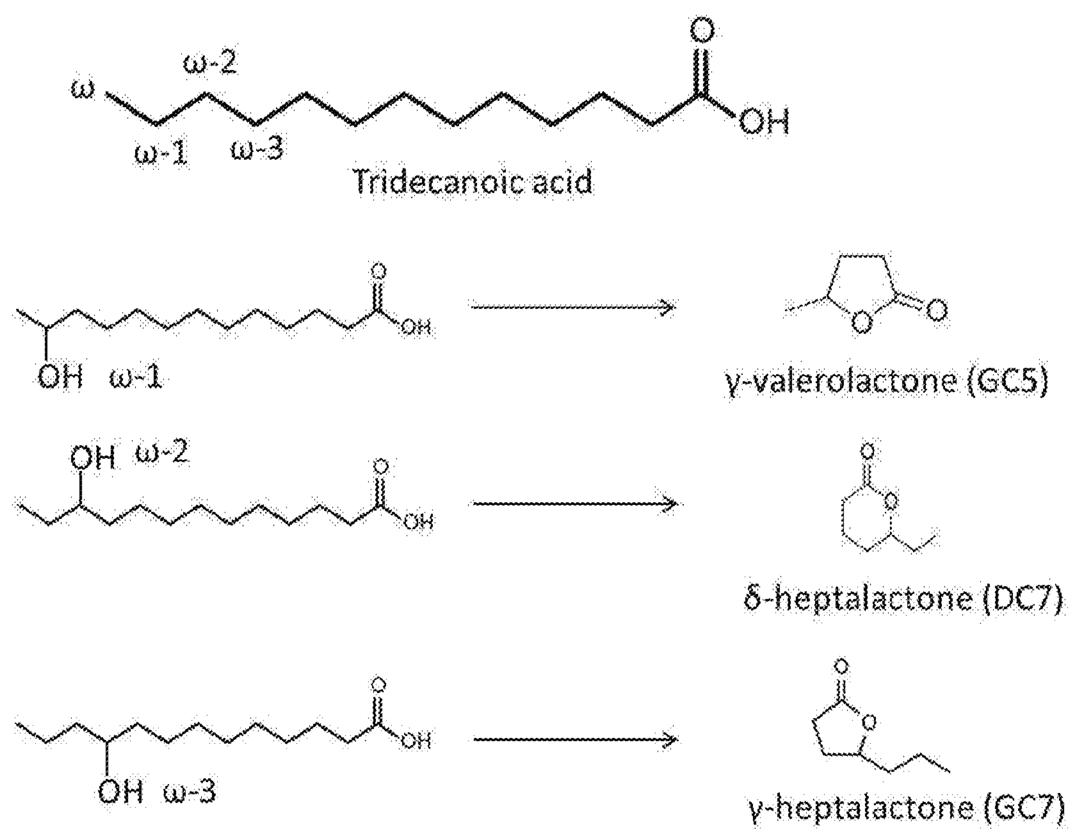
FIG. 5 illustrates the production of γ-valerolactone (GC5), δ-heptalactone (DC7), and γ-heptalactone (GC7) from tridecanoic acid (C13:0).
Figure 6A:
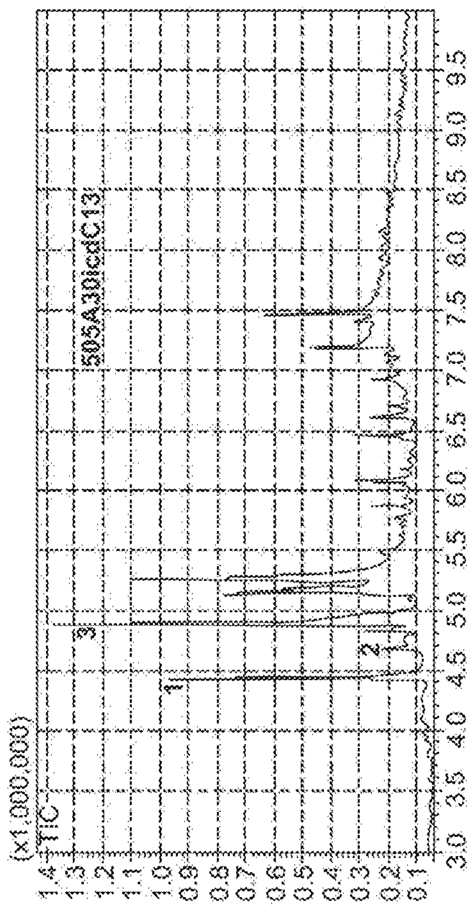
FIGS. 6A, 6B, 6C, and 6D show GC/MS spectra confirming production of gamma- and delta-lactones from subterminal hydroxy fatty acids HO-13:0. Peaks are identified based on the retention times and mass spectra of the peaks compared with standards from Sigma.
Figure 6B:
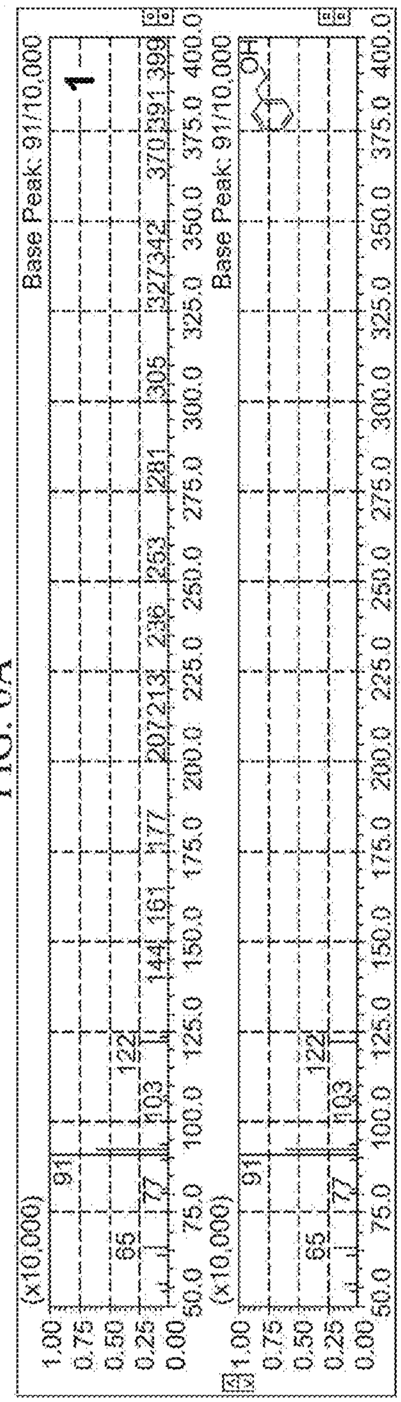
Figure 6C:
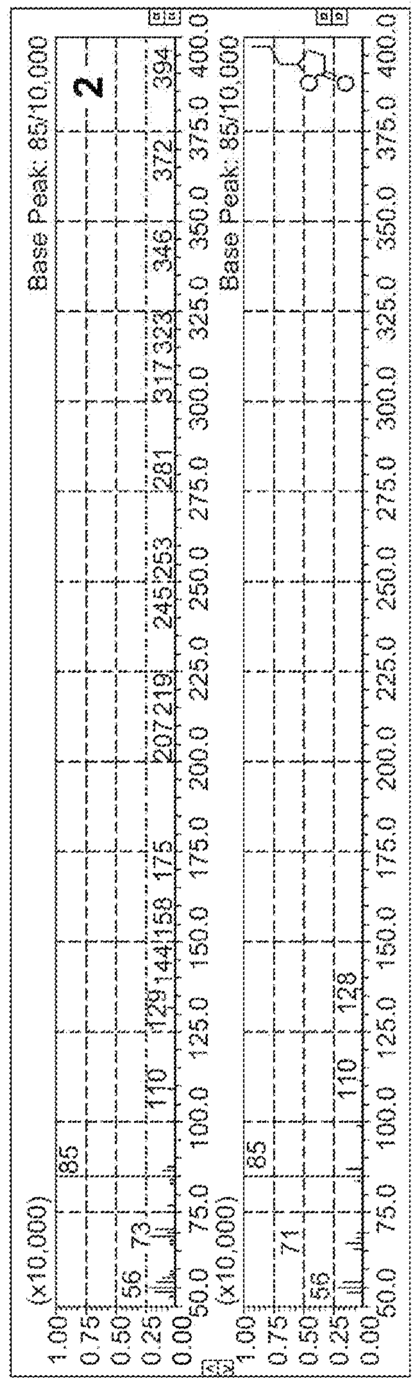
Figure 6D:
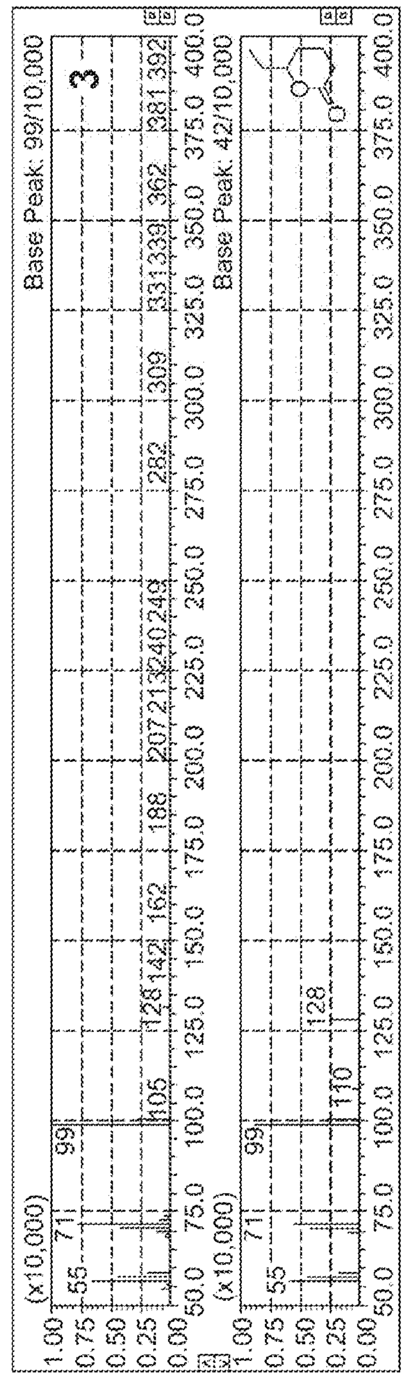

As shown in FIG. 5, if the initial starting fatty acid has an odd number of carbons such as C13:0 (tridecanoic acid, also known as tridecylic acid), after β-oxidation in yeast, the predicted products would be γ-valerolactone (GC5) from the ω-1 hydroxy fatty acid intermediate, δ-heptalactone (DC7) from the ω-2 hydroxy fatty acid intermediate, and γ-heptalactone (GC7) from the ω-3 hydroxy fatty acid intermediate. This is because in each round of β-oxidation, 2 carbon atoms are removed from the hydroxy fatty acid intermediate. Depending on the position of the OH group in the hydroxy fatty acid, there can be 10, 9, or 8 intervening carbon atoms between the hydroxylated carbon atom and the carboxylated carbon atom in the hydroxy fatty acid. Once β-oxidation has removed enough pairs of carbon atoms such that there are either 2 or 3 intervening carbon atoms remaining, favorable kinetics lead to cyclization into the lactone product (a γ-lactone if there are 2 intervening carbon atoms remaining, and a δ-lactone if there are 3 intervening carbon atoms remaining).

FIG. 6 shows the spectra from GC/MS analysis obtained with CYP505A30C13 (containing ω-1 to ω-3 hydroxy tridecanoic acid) following incubation with *Candida boidinii*. Referring to FIG. 6A, peaks 1, 2, 3, and 4 were analyzed. After comparing the retention times to those of known standards, peak 2 was identified to be the γ-heptalactone GC7, and peak 3 was identified to be the δ-heptalactone DC7. Peak 1 was identified to be phenethyl alcohol, which is a metabolite of yeast metabolism. Valerolactone (GC5) was not detected by GC/MS most likely due to its low concentration or volatility.

These results demonstrate production of lactones from hydroxy fatty acids by inoculation with a yeast cell culture.

Example 3

Production of Lactones Using *E. coli* Cells Overexpressing *U. Isabellina* Cytochrome P450 Protein The amino acid sequence of a BM3 homolog from *Umbelopsis isabelline*, a cytochrome P450 protein, was obtained from JGI Genome Portal (www.genome.jgi.doe-.gov/cgi-bin/dispGeneModel?db=Umbisal&id=523695) and the corresponding gene was codon-optimized for expression in *Escherichia coli* and synthesized by Gene Universal Inc. (Newark, DE). The nucleotide sequence of BM3 homolog of *Umbelopsis isabellina*, MI2, with codon-optimization for *E. coli* expression is provided below as SEQ ID NO: 5. The amino acid sequence of MI2 is provided below as SEQ ID NO: 6.

The resulting gene product was cloned into pET-32a-(+) vector (AMP+, Novagen) through HindIII and XhoI sites. The construct was transformed into BL21 (DE3) cells for expression, and an overnight culture was used to inoculate liquid LB medium (2%) containing 100 mg/L of carbenicillin. After 16 h of incubation at 16° C., cells were harvested by centrifugation.

Harvested cell pellets were resuspended at a concentration of 100 g/L fresh weight in 100 mM potassium phosphate buffer (pH7.0) containing 0.1% Tween 40. Then 1 g/L of lauric acid (C12:0) or 1 g/L of tridecanoic acid (C13:0) was added for biotransformation at 30° C. in a shaker. Samples were taken at different reaction times and the production of hydroxy fatty acids were determined by GC/MS after silylation with MSTFA (N-methyl-N-trimethylsilyl-trifluoroacetamide).

Figure 7A:
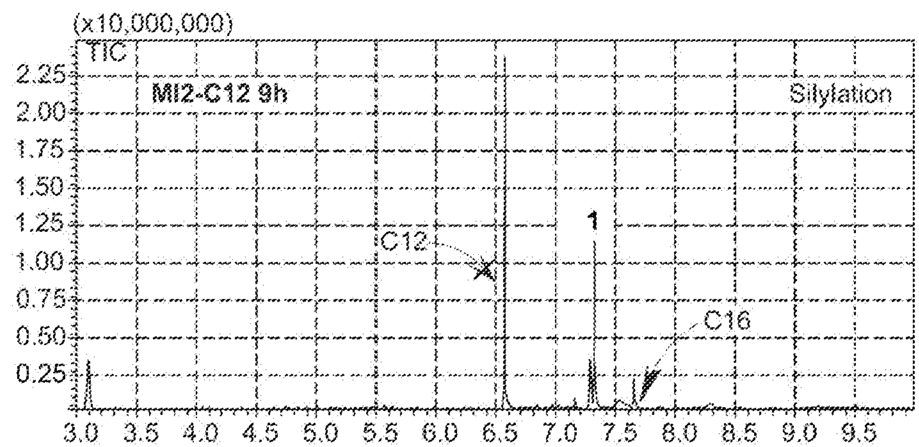
FIGS. 7A and 7B show GC/MS spectra confirming production of subterminal hydroxy fatty acid HO-C12:0 (peak 1 in FIG. 7A) and HO-C13:0 (peak 1 in FIG. 7B) from C12:0 and C13:0, respectively, in a cellular system in which the gene MI2 was overexpressed. Samples were taken 9 h after the bioconversion and silylated with N-Triethylsilyl-N-methyl trifluoroacetamide.
Figure 7B:
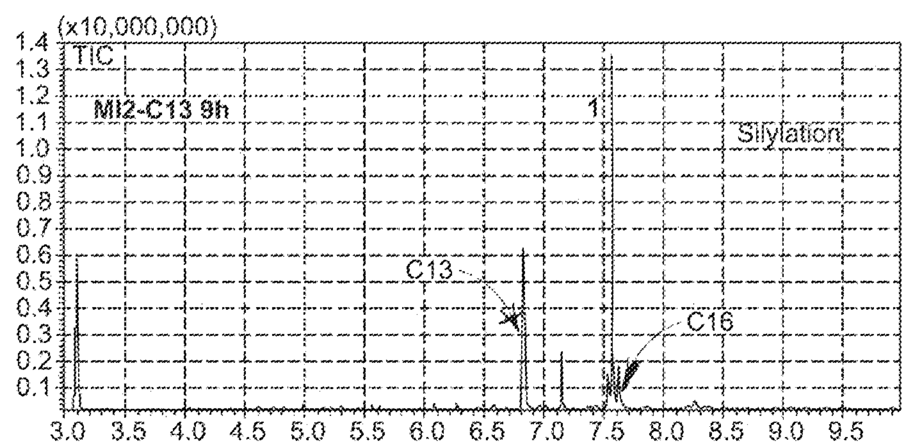

FIG. 7A and FIG. 7B demonstrate production of HO-C12:0 and HO-C13:0 from the corresponding carboxylic acids by *E. coli* cells overexpressing BM3 homolog of *Umbelopsis isabellina*, MI2. Although a mass spectrum library search did not find exact matches for peak 1 in the samples, the search indicated that the peak was hydroxy fatty acids.

To produce lactones from the hydroxy fatty acids HO-C12:0 and HO-C13:0, the biotransformation mixture was mixed with 60 g/L of corn steep liquor (CSL) at 1:1 ratio, and the resulting medium was autoclaved at 121° C. for 20 min. The media was labelled as MI2-C12-CSL or MI2-C13-CSL for C12:0 and C13:0 bioconversion, respectively. Then the medium was inoculated with an overnight yeast culture, e.g., *Candida boidinii* and the yeast culture was grown in a 30° C. shaker. Samples were taken daily after inoculation.

To analyze lactone production in yeast cultures, 0.5 ml *Candida boidinii* culture was taken and 10 μl 2N HCl was added. The acidified culture was extracted with 0.5 ml ethyl acetate with shaking at room temperature for 60 min. After centrifugation at 14,000 rpm for 15 min, the ethyl acetate phase was used for GC/MS or GC/FID analysis.

Figure 8A:
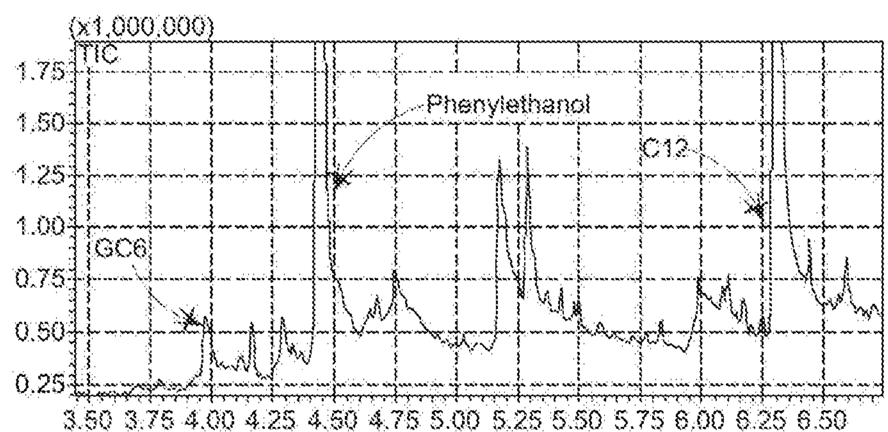
FIGS. 8A and 8B show GC/MS spectra confirming lactone production from different hydroxy fatty acids.
Figure 8B:
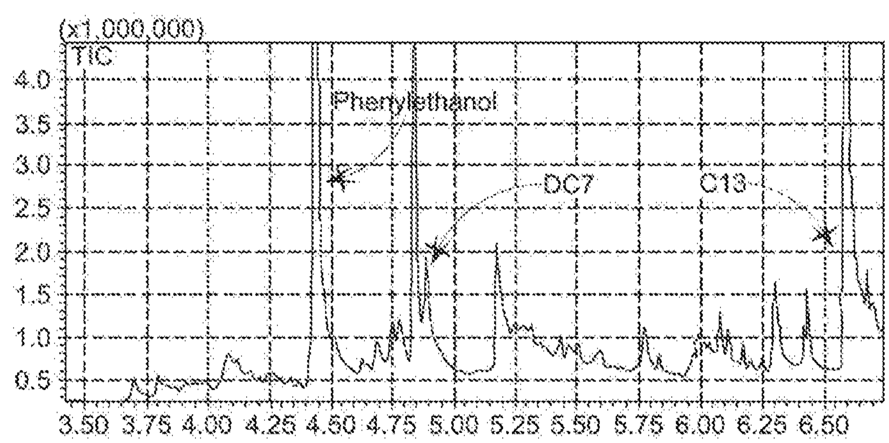

FIG. 8A and FIG. 8B demonstrate that GC6 is the major lactone derived from C12:0 (via HO-C12:0 as an intermediate) and DC7 is the major lactone derived from C13:0 (via HO-C13:0 as an intermediate), respectively. This suggests that ω-2 hydroxy lauric acid and ω-2 hydroxy tridecanoic acid likely correspond to peak 1 in FIG. 7A and FIG. 7B, respectively, which in turn were derived from C12 and C13, respectively.

Taken together, these results demonstrate that *Umbelopsis isabellina* cytochrome P450 MI2 is an ω-2 fatty acid hydroxylase and can be used for production of γ-hexalactone or 8-heptalactone.

Sequences of Importance

*M. thermophile* CYP505A30 nucleotide sequence (SEQ ID NO: 1)

```
ATGGCGGATAAGACCACCGAAACCGTGCCGATTCCGGGTCCGCCGGGCCTG
CCGCTGGTTGGTAATGCGCTGGCGTTTGATAGCGAACTGCCGCTGCGTACC
TTCCAGGAATTTGCGGAGGAATACGGCGAGATCTATCGTCTGACCCTGCCG
ACCGGTACCACCCTGGTGGTTAGCAGCCAAGCGCTGGTTCACGAACTGTGC
GACGATAAGCGTTTCAAGAAGCCGGTTGCTGCGGCGCTGGCGGAAGTGCGT
AACGGCGTTAACGACGGTCTGTTTACCGCGCGTGAAGAGGAGCCGAACTGG
GGCATCGCGCACCGTATTCTGATGCCGGCGTTTGGTCCGGCGAGCATTCAG
GGC
ATGTTTACCGAAATGCACGAGATCGCGAGCCAACTGGCGCTGAAATGGGCG
CGTCACGGTCCGGACACCCCGATTTTCGTTACCGACGATTTTACCCGTCTG
ACCCTGGATACCCTGGCGCTGTGCACCATGAACTTCCGTTTTAACAGCTAC
TATCACGACGAACTGCACCCGTTCATCAACGCGATGGGCAACTTTCTGACC
GAGAGCGGTGCGCGTGCGATGCGTCCGGCGATCACCAGCATTTTCCACCAG
GCGGCGAACCGTAAGTACTGGGAAGATATTGAGGTTCTGCGTAAAACCGCG
CAAGGTGTGCTGGACACCCGTCGTAAGCACCCGACCAACCGTAAAGATCTG
CTGAGCGCGATGCTGGACGGCGTGGATGCGAAAACCGGTCAGAAACTGAGC
GACAGCAGCATCATTGATAACCTGATCACCTTTCTGATTGCGGGCCACGAA
```

-continued

```
ACCACCAGCGGTCTGCTGAGCTTCGCGTTTTACCTGCTGATTAAGCACCAG
GACGCGTATCGTAAAGCGCAAGAAGAGGTGGATCGTGTTATCGGCAAGGGC
CCGATTAAAGTTGAACACATCAAGAAACTGCCGTACATCGCGGCGGTGCTG
CGTGAAACCCTGCGTCTGTGCCCGACCATTCCGATCATTAACCGTGCGGCG
GAAGTTATCGGTGGCAAGTACGCGGTGGCGAAAGATCAGCGTCTGGCGCTG
CTGCTAAGCAGGACGGCGCAAAGCCACCTGGACCCGGCGGTTTATGGCGAA
ACCGCGAAGCAATTCATTCCGGAGCGTATGCTGGACGAAAACTTTGAGCGT
CTGAACCGTGAGTATCCGGATTGCTGGAAACCGTTCGGTACCGGCATGCGT
GCGTGCATCGGTCGTCCGTTTGCGTGGCAGGAAGCGGTGCTGGTTATGGCG
ATGCTGCTGCAAAACTTCGACTTTGTTCTGCACGATCCGTACTATGAGCTG
CACTACAAGCAGACCCTGACCACCAAGCCGAAAGACTTCTATATGCGTGCG
ATCCTGCGTGATGGCCTGACCGCGACCGAACTGGAGCACCGTCTGGCGGGT
AACGCGGCGAGCGTGGCGCGTAGCGGTGGCGGTGGCGGTGGCCCGAGCAAA
CCGACCGCGCAGAAAACCAGCCCGGCGGAAGCGAAACCGATGAGCATCTTC
TACGGCAGCAACACCGGTACCTGCGAGAGCCTGGCGCAACGTCTGGCGACC
GATGCGGCGAGCCACGGTTATGCTGCGGCGGCGGTGGAACCGCTGGACACC
GCGACCGAGAAGCTGCCGACCGATCGTCCGGTGGTTATCATTACCGCGAGC
TTCGAGGGTCAGCCGCCGGACAACGCGGCGAAGTTTTGCGGCTGGCTGAAA
AACCTGGAAGGTGATGAGCTGAAAAACGTGAGCTACGCGGTTTTCGGTTGC
GGCCACCACGACTGGAGCCAGACCTTTCACCGTATTCCGAAGCTGGTTCAC
CAAACCATGAAAGCGCACGGTGCGAGCCCGATCTGCGACGAAGGCCTGACC
GATGTGGCGGAGGGTAACATGTTCACCGATTTTGAACAATGGGAGGACGAT
GTGTTCTGGCCGGCGGTTCGTGCGCGTTATGGCGCGGCGGGTGCGGTTGCG
GAAACCGAGGACGCGCCGGGTAGCGATGGTCTGAACATCCACTTTAGCAGC
CCGCGTAGCAGCACCCTGCGTCAGGACGTGCGTGAAGCGACCGTGGTTGGT
GAAGCGCTGCTGACCGCGCCGGATGCGCCGCCGAAGAAACACATTGAAGTT
CAACTGCCGGACGGCGCGACCTACAAAGTGGGTGATTATCTGGCGGTGCTG
CCGGTTAACAGCAAGGAGAGCATTGGTCGTGTTATGCGTAAATTCCAGCTG
AGCTGGGACAGCCACGTGACCATCGCGAGCGATCGTTGGACCGCGCTGCCG
ACCGGTACCCCGGTGCCGGCGTACGACGTTCTGGGTAGCTATGTGGAGCTG
AGCCAACCGGCGACCAAACGTGGTATCCTGCGTCTGGCGGATGCGGCGGAA
GATGAGGCGACCAAGGCGGAACTGCAAAAACTGGCGGGTGATCTGTACACC
AGCGAGATTAGCCTGAAACGTGCGAGCGTTCTGGACCTGCTGGATCGTTTC
CCGAGCATCAGCCTGCCGTTCGGTACCTTTCTGAGCCTGCTGCCGCCGATT
CGTCCGCGTCAATACAGCATCAGCAGCAGCCCGCTGAACGACCCGAGCCGT
GCGACCCTGACCTATAGCCTGCTGGATAGCCCGAGCCTGGCGAACCCGAGC
CGTCGTTTCGTGGGCGTTGCGACCAGCTACCTGAGCAGCCTGGTTCGTGGT
GACAAGCTGCTGGTGAGCGTTCGTCCGACCCACACCGCGTTTCGTCTGCCG
GACGAAGATAAAATGGGTGAAACCGCGATCATTTGCGTGGGTGCGGGTAGC
GGTCTGGCGCCGTTCCGTGGTTTTATCCAGGAACGTGCGGCGCTGCTGGCG
```

-continued

AAAGGTACCCAACTGGCGGCGGCGCTGCTGTTCTACGGTTGCCGTAGCCCG

GAGAAGGACGATCTGTATCGTGACGAATTCGATAAATGGCAAGAGAGCGGT

GCGGTGGATGTTCGTCGTGCGTTTAGCCGTGTTGATAGCGACGATACCGAG

GCGCGTGGTTGCCGTCACGTTCAGGACCGTCTGTGGCACGATCGTGAAGAG

GTGAAGGCGCTGTGGGACCGTGGCGCGCGTGTGTACGTTTGCGGTAGCCGT

CAAGTGGGCGAAGGTGTTAAAACCGCGATGGGCCGTATCGTGCTGGGTGAA

GAGGACGCGGAGGATGCGATCAGCAAGTGGTATGAAACCGTGCGTAATGAC

CGTTATGCGACCGATGTGTTCGACTAA icd gene from *E. coli* K-12 substr. MG1655
(SEQ ID NO: 2)

GAAAGTAAAGTAGTTGTTCCGGCACAAGGCAAGAAGATCACCCTGCAAAAC

GGCAAACTCAACGTTCCTGAAAATCCGATTATCCCTTACATTGAAGGTGAT

GGAATCGGTGTAGATGTAACCCCAGCCATGCTGAAAGTGGTCGACGCTGCA

GTCGAGAAAGCCTATAAAGGCGAGCGTAAAATCTCCTGGATGGAAATTTAC

ACCGGTGAAAAATCCACACAGGTTTATGGTCAGGACGTCTGGCTGCCTGCT

GAAACTCTTGATCTGATTCGTGAATATCGCGTTGCCATTAAAGGTCCGCTG

ACCACTCCGGTTGGTGGCGGTATTCGCTCTCTGAACGTTGCCCTGCGCCAG

GAACTGGATCTCTACATCTGCCTGCGTCCGGTACGTTACTATCAGGGCACT

CCAAGCCCGGTTAAACACCCTGAACTGACCGATATGGTTATCTTCCGTGAA

AACTCGGAAGACATTTATGCGGGTATCGAATGGAAAGCAGACTCTGCCGAC

GCCGAGAAAGTGATTAAATTCCTGCGTGAAGAGATGGGGGTGAAGAAAATT

CGCTTCCCGGAACATTGTGGTATCGGTATTAAGCCGTGTTCGGAAGAAGGC

ACCAAACGTCTGGTTCGTGCAGCGATCGAATACGCAATTGCTAACGATCGT

GACTCTGTGACTCTGGTGCACAAAGGCAACATCATGAAGTTCACCGAAGGA

GCGTTTAAAGACTGGGGCTACCAGCTGGCGCGTGAAGAGTTTGGCGGTGAA

CTGATCGACGGTGGCCCGTGGCTGAAAGTTAAAAACCCGAACACTGGCAAA

GAGATCGTCATTAAAGACGTGATTGCTGATGCATTCCTGCAACAGATCCTG

CTGCGTCCGGCTGAATATGATGTTATCGCCTGTATGAACCTGAACGGTGAC

TACATTTCTGACGCCCTGGCAGCGCAGGTTGGCGGTATCGGTATCGCCCCT

GGTGCAAACATCGGTGACGAATGCGCCCTGTTTGAAGCCACCCACGGTACT

GCGCCGAAATATGCCGGTCAGGACAAAGTAAATCCTGGCTCTATTATTCTC

TCCGCTGAGATGATGCTGCGCCACATGGGTTGGACCGAAGCGGCTGACTTA

ATTGTTAAAGGTATGGAAGGCGCAATCAACGCGAAAACCGTAACCTATGAC

TTCGAGCGTCTGATGGATGGCGCTAAACTGCTGAAATGTTCAGAGTTTGGT

GACGCGATCATCGAAAACATGTAA

*M. thermophile* CYP505A30 amino acid sequence
(SEQ ID NO: 3)

MADKTTETVPIPGPPGLPLVGNALAFDSELPLRTFQEFAEEYGEIYRLTLP

TGTTLVVSSQALVHELCDDKRFKKPVAAALAEVRNGVNDGLFTAREEEPNW

GIAHRILMPAFGPASIQGMFTEMHEIASQLALKWARHGPDTPIFVTDDFTR

LTLDTLALCTMNFRFNSYYHDELHPFINAMGNFLTESGARAMRPAITSIFH

QAANRKYWEDIEVLRKTAQGVLDTRRKHPTNRKDLLSAMLDGVDAKTGQKL

SDSSIIDNLITFLIAGHETTSGLLSFAFYLLIKHQDAYRKAQEEVDRVIGK

-continued

GPIKVEHIKKLPYIAAVLRETLRLCPTIPIINRAAKQDEVIGGKYAVAKDQ

RLALLLAQSHLDPAVYGETAKQFIPERMLDENFERLNREYPDCWKPFGTGM

RACIGRPFAWQEAVLVMAMLLQNFDFVLHDPYYELHYKQTLTTKPKDFYMR

AILRDGLTATELEHRLAGNAASVARSGGGGGGPSKPTAQKTSPAEAKPMSI

FYGSNTGTCESLAQRLATDAASHGYAAAAVEPLDTATEKLPTDRPVVIITA

SFEGQPPDNAAKFCGWLKNLEGDELKNVSYAVFGCGHHDWSQTFHRIPKLV

HQTMKAHGASPICDEGLTDVAEGNMFTDFEQWEDDVFWPAVRARYGAAGAV

AETEDAPGSDGLNIHFSSPRSSTLRQDVREATVVGEALLTAPDAPPKKHIE

VQLPDGATYKVGDYLAVLPVNSKESIGRVMRKFQLSWDSHVTIASDRWTAL

PTGTPVPAYDVLGSYVELSQPATKRGILRLADAAEDEATKAELQKLAGDLY

TSEISLKRASVLDLLDRFPSISLPFGTFLSLLPPIRPRQYSISSSPLNDPS

RATLTYSLLDSPSLANPSRRFVGVATSYLSSLVRGDKLLVSVRPTHTAFRL

PDEDKMGETAIICVGAGSGLAPFRGFIQERAALLAKGTQLAAALLFYGCRS

PEKDDLYRDEFDKWQESGAVDVRRAFSRVDSDDTEARGCRHVQDRLWHDRE

EVKALWDRGARVYVCGSRQVGEGVKTAMGRIVLGEEDAEDAISKWYETVRN

DRYATDVFD icd protein from *E. coli* K-12 substr. MG1655
(SEQ ID NO: 4)

MESKVVVPAQGKKITLQNGKLNVPENPIIPYIEGDGIGVDVTPAMLKVVDA

AVEKAYKGERKISWMEIYTGEKSTQVYGQDVWLPAETLDLIREYRVAIKGP

LTTPVGGGIRSLNVALRQELDLYICLRPVRYYQGTPSPVKHPELTDMVIFR

ENSEDIYAGIEWKADSADAEKVIKFLREEMGVKKIRFPEHCGIGIKPCSEE

GTKRLVRAAIEYAIANDRDSVTLVHKGNIMKFTEGAFKDWGYQLAREEFGG

ELIDGGPWLKVKNPNTGKEIVIKDVIADAFLQQILLRPAEYDVIACMNLNG

DYISDALAAQVGGIGIAPGANIGDECALFEATHGTAPKYAGQDKVNPGSII

LSAEMMLRHMGWTEAADLIVKGMEGAINAKTVTYDFERLMDGAKLLKCSEF

GDAIIENM

*Umbelopsis isabellina* MI2 nucleotide sequence
(SEQ ID NO: 5)

ATGAGCACCACCACCCTGATTGTGGCCATTAAGGGTACCGATAATGTTGAA

CGTGATGGCGCAATTGTTCGTCTGGATGCCGGCGCCAGTATGGAAACCCTG

CGTCCGCGCATTGCAGAAAAACTGGCCATTAGCAGTGGCATTGAAGATCTG

ATTCTGGAAGATGCAAATGGTGACAATCTGACCACCATTGATCAGGTTCGT

AAACAGCAGACCGTTTTTGTTAATCTGGAAGATCAGATTAAGCTGCCGGCA

GTTCCGGCCCATACCCTGCCGTATTTTGGTAATCTGTATCAGCTGCTGCCG

GATATGCTGGCCGGTTGGCGCAAACTGTTTGATGAATATGGTCCGGTTGTT

AAAGTGAATCTGCTGGGCAATGAAATTATTGGTACCAATGATCCGGCCGTG

GCCGAACTGTGGGTTAAAGAAAGCGAATATTTTACCAAAAAGATCTACGGT

GGCCTGCAGGAAGTTAAAAGTTTTGGCGGCCAGGGTCTGTTTACCACCGAT

AGCGATGATATGGATTGGAAACTGGCACATAAACTGCTGATGCCGGCATTT

TCACCGCGCGCCATTAAGGTTTATCAGCATGAAATGAGCGTGATTGGTCTG

CAGACCATTAAGGTTTTTGAACAGTATAGCCCGGATGAAGAAGTGGAAATT

-continued

CTGCATTGGACCACCAATCTGACCTTTGAAACCATTGGCAAAGTTGGTTTT
GGCTATGATTTTCATCTGCTGGATGATCGTTATGGCGAAAATCATCCGTTT
ATTGAAGCAATGGGTTATTGCATGAAACAGAGCTTTGCCCGTGGCACCCAG
AGCAAACTGATTAAGTATCTGCCGATTGAAGCCAATCGTCGCTATGATCGC
AGTCTGAATCTGATGCATAGCATTGTTGATGAAGTTATTACCCAGCGTAAA
AGCCATCCGCATGCAAGCGAAGATAATAAGGATCTGCTGGATTTTATGCTG
ACCGCACGTGATGAAAATAATCTGGGCCTGAGCGATGAAAATATTCGCGAT
CAGGTTATTACCTTTCTGATTGCCGGCCATGAAACCACCAGCAATACCCTG
GCATGGACCCTGTATGAACTGAGTCGCCATCCGGAAATTGAACAGAAAATT
CTGCAGGAAGTGGTGAATCTGGGCATTACCACCGATTCACTGCCGACCAGC
GAACAGAGCAGTAGCATGAAATATACCTATCAGGTGCTGAAAGAAACCCTG
CGCATGTATAGTCCGCTGCGTGCACTGGCAAAATATTGCAAAAAAGATATT
GTGGTGCCGGGCGGCTATCAGATTAAGGCAGGCGATCGTGTGGCCGTTCAG
CTGAATAGCCTGCATTATAATGAAAAAGTTTACCCGAATCCGACCCAGTAT
GATCCGAGTCGCTGGACCCCGGAAGAAGAACAGAAACGCAGTCGCTTTGCC
TGGCTGCCGTTTAGCACCGGCCCGCGTAGCTGCATTGGTATGGCACTGGCC
CTGCAGGAAGCAAAAACCATTCTGGCAATGATTCTGCTGAAATTTCGCTTT
GTTTATGATGGTCCGCCGATTGGTTATGATCCGAAAAGCCCGACCATTCGT
CCGCTGAATCTGATGATGAAAATTCTGCCGCGTGATAAACTGCCGAGCCCG
ACCGCCGATAATAAGCTGACCCCGGTTGGCAGTCCGAATATTGGTAAAGCC
CAGATGGCAATGCCGACCGCAGCCACCAATGTTGGTACCGCCGAACTGCCG
CCGGTTTTCTTTCTGTATGGTACCCAGACCGGTACCGCCCAGGATTATGCA
AGTCAGCTGGCAAGCCAGGCCAAAAGTTTTGGTTTTAAAGATATTACCCTG
TGTGAAATGGATAAATGGGAAGTGCTGCAGAGCGGCAAATATACCGGTGCC
AAAGAAGAAAAAGATACCCGTGCCCTGGTTGTTATTTGTACCGCAACCTAT
AATGGCAGCCCGCCGGATAGTGCAGAAAATTTTGATAAATTCATTACCGAC
ACCAGCAAAGATAATGATCTGCCGCTGAAAGGCCTGCTGTATACCGTGTTT
GGCCTGGGCAATCGTAATTGGCGCACCTATCAGCAGTTTCCGATTAAGTGC
GATGCCCGTCTGGATGAACTGGGTGGTGAACGCTTTTATGATCTGGGCAGC
GGCAATGCCGATAAAGATATGGATGGTGAATTTCATGATTGGTGCGCCCAT
TTTTGGACCCATACCCTGACCTATTATGGCATTGCAACCCATGAAGGTAGT
GCAAGTCTGGTGCCGGGCCAGAAAACCACCGAAGATCCGACCAGCGGTCTG
GAAATTCGTTTTATTCCGCCGAGCGAAAGCGAAGCCTGGGATAAAGCCGAT
AAAAATGTTAATGGTGACTATAATGCGGAAATTCAGGTGAATCGCGAACTG
CAGAATATTGAACGTAGTAAACGTAGCACCCGCCATATTGAAATTGATATT
AGTAAACTGCAGAGCCCGGATACCGATAAACATCGTTATCTGACCGGTGAC
CATCTGGAAGTGTATCCGGAAAATGCCGATAATGTGGTGGAAAGCATTGCC
CTGGGCTTTGGTCTGATTCTGGATAGTGTGTTTGAAATTACCAGCGTGGAT

-continued

AAAAGTACCGTGAGTAGTCGTAGCCTGGCAGCCAGTATTACCGGCCCGTGT
ACCGTTCGTAATGCCCTGAAATATTATGCCGATATATATAGTGCCCCGAGC
CGTTATCTGCTGGCCTTTTTCGCAGCACGCCTGCAGGATACCCATCCGGAT
GTTGCCGCAAGTTTTAGCGATGTGATTATTCCGGGTGAAAATGGCCAGAAA
GCCTATAATGAATTCATTCAGAAATACCGTAACCTGCTGGATCTGCAGCGC
GGCTTTCCGCTGAAAGAACTGGATCTGAAAGAATTTCTGTGCGCAGTTAGC
GTTATGCAGCCGCGCCGTTATAGCATTGCCAGCAGCCCGCTGAAAGCAGAA
GATACCGCATATCTGGCAGTTGGTGTGGTGGATGATGTGTTTGCAAATCGT
CATTATTATGGCCTGGCCAGTGGCTATCTGGCCCGCAGCCAGCCGCCGACA
CCGATTCGTGCACGTATTAAGAGTAGCAAAAGTACCTTTGGCCTGCCGGAA
AATCCGGAAACCCCGATTATTATGATTGGTGCCGGTACCGGTATTAGTCCG
TTTATGGGCTTTATGCAGGAACGCGAAATGCTGAAAAGCAAAGCAGAAGCC
CATCTGTTTTTCGGCTGCCGCCATCCGGATGAAGATTTTATCTATCGTAGC
GTTTTTGAAGGCTATGAAAAAAGCGGCGTTATTACCAAACTGTATCCGGCC
TTTAGCCGTCTGGGTGAAGATAATCCGCGCAAATATGTTCAGCATCAGCTG
ATGGCAAATGCCGGCAAAATTTGGACCCTGCTGACCAATGGCGCAAATGTG
TATGTTTGCGGCAGTGGCCCGATGAGCCGCGATGTGCGTCGTAGCTTTGAA
CTGATGGCAAAAAGTTTTGGAGGCGCCAAAACCGATGATGAAGCATGCGAA
AAACTGCTGGAATTCATGAGCGCAGGTCGTTATAATGAAGATGTGTGGGGT
TAA

*Umbelopsis isabellina* MI2 amino acid sequence
(SEQ ID NO: 6)

MSTTTLIVAIKGTDNVERDGAIVRLDAGASMETLRPRIAEKLAISSGIEDL
ILEDANGDNLTTIDQVRKQQTVFVNLEDQIKLPAVPAHTLPYFGNLYQLLP
DMLAGWRKLFDEYGPVVKVNLLGNEIIGTNDPAVAELWVKESEYFTKKIYG
GLQEVKSFGGQGLFTTDSDDMDWKLAHKLLMPAFSPRAIKVYQHEMSVIGL
QTIKVFEQYSPDEEVEILHWTTNLTFETIGKVGFGYDFHLLDDRYGENHPF
IEAMGYCMKQSFARGTQSKLIKYLPIEANRRYDRSLNLMHSIVDEVITQRK
SHPHASEDNKDLLDFMLTARDENNLGLSDENIRDQVITFLIAGHETTSNTL
AWTLYELSRHPEIEQKILQEVVNLGITTDSLPTSEQSSSMKYTYQVLKETL
RMYSPLRALAKYCKKDIVVPGGYQIKAGDRVAVQLNSLHYNEKVYPNPTQY
DPSRWTPEEEQKRSRFAWLPFSTGPRSCIGMALALQEAKTILAMILLKFRF
VYDGPPIGYDPKSPTIRPLNLMMKILPRDKLPSPTADNKLTPVGSPNIGKA
QMAMPTAATNVGTAELPPVFFLYGTQTGTAQDYASQLASQAKSFGFKDITL
CEMDKWEVLQSGKYTGAKEEKDTRALVVICTATYNGSPPDSAENFDKFITD
TSKDNDLPLKGLLYTVFGLGNRNWRTYQQFPIKCDARLDELGGERFYDLGS
GNADKDMDGEFHDWCAHFWTHTLTYYGIATHEGSASLVPGQKTTEDPTSGL
EIRFIPPSESEAWDKADKNVNGDYNAEIQVNRELQNIERSKRSTRHIEIDI
SKLQSPDTDKHRYLTGDHLEVYPENADNVVESIALGFGLILDSVFEITSVD
KSTVSSRSLAASITGPCTVRNALKYYADIYSAPSRYLLAFFAARLQDTHPD
VAASFSDVIIPGENGQKAYNEFIQKYRNLLDLQRGFPLKELDLKEFLCAVS

-continued

VMQPRRYSIASSPLKAEDTAYLAVGVVDDVFANRHYYGLASGYLARSQPPT

PIRARIKSSKSTFGLPENPETPIIMIGAGTGISPFMGFMQEREMLKSKAEA

HLFFGCRHPDEDFIYRSVFEGYEKSGVITKLYPAFSRLGEDNPRKYVQHQL

MANAGKIWTLLTNGANVYVCGSGPMSRDVRRSFELMAKSFGGAKTDDEACE

KLLEFMSAGRYNEDVWG

ICD-F Primer (SEQ ID No: 7)

GGAATTCCATATGGAAAGTAAAGTAGTTGT

ICD-R Primer (SEQ ID No: 8)

CCGCTCGAGTTACATGTTTTCGATGATCGCGT

TABLE 1

| Examples of fatty acids | | | |
|---|---|---|---|
| Common Name | Systematic Name | Structural Formula | Lipid Numbers |
| Valeric acid | Pentanoic acid | $CH_3(CH_2)_3COOH$ | C5:0 |
| Caproic acid | Hexanoic acid | $CH_3(CH_2)_4COOH$ | C6:0 |
| Enanthic acid | Heptanoic acid | $CH_3(CH_2)_5COOH$ | C7:0 |
| Caprylic acid | Octanoic acid | $CH_3(CH_2)_6COOH$ | C8:0 |
| Pelargonic acid | Nonanoic acid | $CH_3(CH_2)_7COOH$ | C9:0 |
| Capric acid | Decanoic acid | $CH_3(CH_2)_8COOH$ | C10:0 |
| Undecylic acid | Undecanoic acid | $CH_3(CH_2)_9COOH$ | C11:0 |
| Lauric acid | Dodecanoic acid | $CH_3(CH_2)_{10}COOH$ | C12:0 |
| Tridecylic acid | Tridecanoic acid | $CH_3(CH_2)_{11}COOH$ | C13:0 |
| Myristic acid | Tetradecanoic acid | $CH_3(CH_2)_{12}COOH$ | C14:0 |
| Pentadecylic acid | Pentadecanoic acid | $CH_3(CH_2)_{13}COOH$ | C15:0 |
| Palmitic acid | Hexadecanoic acid | $CH_3(CH_2)_{14}COOH$ | C16:0 |
| Margaric acid | Heptadecanoic acid | $CH_3(CH_2)_{15}COOH$ | C17:0 |
| Stearic acid | Octadecanoic acid | $CH_3(CH_2)_{16}COOH$ | C18:0 |
| Nonadecylic acid | Nonadecanoic acid | $CH_3(CH_2)_{17}COOH$ | C19:0 |
| Arachidic acid | Eicosanoic acid | $CH_3(CH_2)_{18}COOH$ | C20:0 |
| Heneicosylic acid | Heneicosanoic acid | $CH_3(CH_2)_{19}COOH$ | C21:0 |
| Behenic acid | Docosanoic acid | $CH_3(CH_2)_{20}COOH$ | C22:0 |
| Tricosylic acid | Tricosanoic acid | $CH_3(CH_2)_{20}COOH$ | C23:0 |
| Lignoceric acid | Tetracosanoic acid | $CH_3(CH_2)_{22}COOH$ | C24:0 |
| Pentacosylic acid | Pentacosanoic acid | $CH_3(CH_2)_{23}COOH$ | C25:0 |
| Cerotic acid | Hexacosanoic acid | $CH_3(CH_2)_{24}COOH$ | C26:0 |
| Heptacosylic acid | Heptacosanoic acid | $CH_3(CH_2)_{25}COOH$ | C27:0 |
| Montanic acid | Octacosanoic acid | $CH_3(CH_2)_{26}COOH$ | C28:0 |
| Nonacosylic acid | Nonacosanoic acid | $CH_3(CH_2)_{27}COOH$ | C29:0 |
| Melissic acid | Triacontanoic acid | $CH_3(CH_2)_{28}COOH$ | C30:0 |
| Henatriacontylic acid | Henatriacontanoic acid | $CH_3(CH_2)_{29}COOH$ | C31:0 |
| Lacceroic acid | Dotriacontanoic acid | $CH_3(CH_2)_{30}COOH$ | C32:0 |
| Psyllic acid | Tritriacontanoic acid | $CH_3(CH_2)_{31}COOH$ | C33:0 |
| Geddic acid | Tetratriacontanoic acid | $CH_3(CH_2)_{32}COOH$ | C34:0 |
| Ceroplastic acid | Pentatriacontanoic acid | $CH_3(CH_2)_{33}COOH$ | C35:0 |
| Hexatriacontylic acid | Hexatriacontanoic acid | $CH_3(CH_2)_{34}COOH$ | C36:0 |
| Heptatriacontanoic acid | Heptatriacontanoic acid | $CH_3(CH_2)_{35}COOH$ | C37:0 |
| Octatriacontanoic acid | Octatriacontanoic acid | $CH_3(CH_2)_{36}COOH$ | C38:0 |
| Nonatriacontanoic acid | Nonatriacontanoic acid | $CH_3(CH_2)_{37}COOH$ | C39:0 |
| Tetracontanoic acid | Tetracontanoic acid | $CH_3(CH_2)_{38}COOH$ | C40:0 |

TABLE 2

| Sequence Information | |
|---|---|
| Seq ID No. | Sequence Description |
| 1 | *M. thermophile* CYP505A30 nucleotide sequence with codon-optimization for *E. coli* |
| 2 | icd gene from *E. coli* K-12 substr. MG1655 |
| 3 | *M. thermophile* CYP505A30 amino acid sequence |
| 4 | icd protein from *E. coli* K-12 substr. MG1655 |
| 5 | *Umbelopsis isabellina* MI2 BM3 homolog nucleotide sequence codon-optimization for *E. coli* expression |
| 6 | *Umbelopsis isabellina* MI2 BM3 homolog amino acid sequence |
| 7 | ICD-F Primer 5'GGAATTCCATATGGAAAGTAAAGTAGTTGT3' |
| 8 | ICD-R Primer 5'CCGCTCGAGTTACATGTTTTCGATGATCGCGT3' |

What is claimed is:

1. A method of making lactones, the method comprising:

(a) incubating a cellular system expressing a heterologous cytochrome P450 (CYP450) protein with a medium comprising a straight chain fatty acid to produce a subterminal hydroxy fatty acid, wherein the straight chain fatty acid and the subterminal hydroxy fatty acid have 5 to 40 carbon atoms, and wherein the heterologous cytochrome P450 protein comprises an amino acid sequence that is at least 90% identical to the amino acid sequence of a cytochrome P450 protein from *Umbelopsis isabellina*, and either:

(b1) incubating the subterminal hydroxy fatty acid with a yeast cell culture to produce lactones, wherein the lactones comprise at least one gamma-lactone, at least one delta-lactone, or combinations thereof, or (b2) incubating the subterminal hydroxy fatty acids in an acidic environment to produce lactones, wherein the lactones comprise at least one gamma-lactone, at least one delta-lactone, or combinations thereof.

2. The method of claim 1, wherein the heterologous cytochrome P450 protein comprises the amino acid sequence of SEQ ID NO: 6.

3. The method of claim 1, wherein the cellular system expresses an exogenous isocitrate dehydrogenase (Icd) protein besides expressing an heterogenous cytochrome 450 protein.

4. The method of claim 3, wherein the Icd protein comprises an amino acid sequence that is at least 95% identical to the amino acid sequence of an Icd protein from *E. coli*.

5. The method of claim 3, wherein the Icd protein comprises the amino acid sequence of SEQ ID NO: 4.

6. The method of claim 1, wherein the straight chain fatty acid and the hydroxy fatty acid have 7 carbons to 20 carbons.

7. The method of claim 1, wherein the straight chain fatty acid is lauric acid or tridecylic acid.

8. The method of claim 1, wherein the subterminal hydroxy fatty acid is a hydroxylated lauric acid, or a hydroxylated tridecylic acid.

9. The method of claim 1, wherein the cellular system comprises bacterial cells, yeast cells, or a combination thereof.

10. The method of claim 1, wherein the lactones comprise five carbons to eight carbons.

11. The method of claim 1, wherein the lactones comprise one or more of δ-hexalactone, γ-hexalactone, and δ-octalactone.

12. The method of claim 1, wherein the lactones comprise one or more of γ-valerolactone, δ-heptalactone, and γ-heptalactone.

13. The method of claim 1, wherein the straight chain fatty acid is lauric acid, the subterminal hydroxyl fatty acid comprises one or more of ω-1 hydroxy lauric acid, ω-2 hydroxy lauric acid, and ω-3 hydroxy lauric acid, and the lactones comprise one or more of δ-hexalactone, γ-hexalactone, and δ-octalactone.

14. The method of claim 1, wherein the straight chain fatty acid is tridecylic acid, the subterminal hydroxy fatty acid comprises one or more of ω-1 hydroxy tridecylic acid, ω-2 hydroxy tridecylic acid, and ω-3 hydroxy tridecylic acid, and the lactones comprise one or more of γ-valerolactone, δ-heptalactone, and γ-heptalactone.

15. The method of claim 1, wherein the subterminal hydroxy fatty acid is isolated from the cellular system prior to step (b1) or (b2).

16. The method of claim 1, further comprising isolating the lactones from the yeast cell culture.

17. A method of making lactones, the method comprising:

(a) incubating a cellular system expressing a heterologous cytochrome P450 protein with a medium comprising a straight chain fatty acid to produce a subterminal hydroxy fatty acid, wherein the heterologous cytochrome P450 protein comprises an amino acid sequence that is at least 90% identical to the amino acid sequence of a cytochrome P450 protein from *Umbelopsis isabellina*; and wherein the straight chain fatty acid and the subterminal hydroxy fatty acid have 5 to 40 carbon atoms;

(b) incubating the subterminal hydroxy fatty acid from step (a) with a cell culture to produce subterminal hydroxy fatty acid with the length shorter than the subterminal hydroxy fatty acid from step (a); and (c) incubating the subterminal hydroxy fatty acids obtained at the end of step (b) in an acidic environment to produce lactones, wherein the lactones comprise at least one gamma-lactone, at least one delta-lactone, or combinations thereof.

* * * * *